(12) United States Patent
Ellson et al.

(10) Patent No.: US 6,746,104 B2
(45) Date of Patent: *Jun. 8, 2004

(54) METHOD FOR GENERATING MOLECULAR ARRAYS ON POROUS SURFACES

(75) Inventors: Richard N. Ellson, Palo Alto, CA (US); Mitchell W. Mutz, Palo Alto, CA (US); James K. Foote, Cupertino, CA (US)

(73) Assignee: Picoliter Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/964,215

(22) Filed: Sep. 25, 2001

(65) Prior Publication Data

US 2002/0037527 A1 Mar. 28, 2002

Related U.S. Application Data

(63) Continuation-in-part of application No. 09/727,392, filed on Nov. 29, 2000, now abandoned, which is a continuation-in-part of application No. 09/669,996, filed on Sep. 25, 2000, now abandoned.

(51) Int. Cl.[7] .................................................. B41J 2/135
(52) U.S. Cl. .............................. 347/46; 435/6; 435/7.1; 436/180
(58) Field of Search .......................... 435/6, 7.1, 287.2, 435/DIG. 49; 436/180, 524–530; 347/46; 205/81

(56) References Cited

U.S. PATENT DOCUMENTS

| | | |
|---|---|---|
| 4,308,547 A | 12/1981 | Lovelady et al. |
| 4,697,195 A | 9/1987 | Quate et al. |
| 4,719,476 A | 1/1988 | Elrod et al. |
| 4,751,529 A | 6/1988 | Elrod et al. |
| 4,751,530 A | 6/1988 | Elrod et al. |
| 4,751,534 A | 6/1988 | Elrod et al. |
| 4,797,693 A | 1/1989 | Quate |
| 4,801,953 A | 1/1989 | Quate |
| 4,959,674 A | 9/1990 | Khri-Yakub et al. |
| 5,087,931 A | 2/1992 | Rawson |
| 5,122,818 A | 6/1992 | Elrod et al. |
| 5,216,451 A | 6/1993 | Rawson et al. |
| 5,229,016 A | 7/1993 | Hayes et al. |
| 5,229,793 A | 7/1993 | Hadimioglu et al. |
| 5,231,426 A | 7/1993 | Sweet |
| 5,339,101 A | 8/1994 | Rawson et al. |
| 5,377,902 A | 1/1995 | Hayes |
| 5,392,064 A | 2/1995 | Hadimioglu et al. |
| 5,415,679 A | 5/1995 | Wallace |
| 5,436,327 A | 7/1995 | Southern et al. |
| 5,498,444 A | 3/1996 | Hayes |
| 5,520,715 A | 5/1996 | Oeftering |
| 5,556,752 A | 9/1996 | Lockhart et al. |
| 5,591,490 A | 1/1997 | Quate |
| 5,608,433 A | 3/1997 | Quate |
| 5,629,724 A | 5/1997 | Elrod et al. |
| 5,631,678 A | 5/1997 | Hadimioglu et al. |
| 5,643,353 A | 7/1997 | Wallace et al. |
| 5,658,802 A | 8/1997 | Hayes et al. |
| 5,722,479 A | 3/1998 | Oeftering |
| 5,744,305 A | 4/1998 | Fodor et al. |
| 5,798,779 A | 8/1998 | Nakayasu et al. |
| 5,808,636 A | 9/1998 | Stearns |
| 5,959,297 A | 9/1999 | Weinberg et al. |
| 5,985,356 A | 11/1999 | Schultz et al. |
| 6,004,617 A | 12/1999 | Schultz et al. |
| 6,010,316 A | 1/2000 | Haller et al. |
| 6,015,880 A | 1/2000 | Baldeschwieler et al. |
| 6,028,189 A | 2/2000 | Blanchard |
| 6,029,896 A | 2/2000 | Self et al. |
| 6,030,917 A | 2/2000 | Weinberg et al. |
| 6,034,775 A | 3/2000 | McFarland et al. |
| 6,045,671 A | 4/2000 | Wu et al. |
| 6,087,181 A | 7/2000 | Cong |
| 6,187,164 B1 | 2/2001 | Warren et al. |
| 6,548,308 B2 * | 4/2003 | Ellson et al. ................ 436/180 |
| 6,596,239 B2 * | 7/2003 | Williams et al. ............ 422/100 |
| 6,612,686 B2 * | 9/2003 | Mutz et al. .................... 347/46 |
| 2002/0037359 A1 | 3/2002 | Mutz et al. |
| 2002/0037527 A1 | 3/2002 | Ellson et al. |
| 2002/0037579 A1 * | 3/2002 | Ellson et al. ............. 435/287.2 |
| 2002/0042077 A1 | 4/2002 | Ellson |
| 2002/0061598 A1 | 5/2002 | Mutz et al. |

FOREIGN PATENT DOCUMENTS

WO    WO 01/52991    7/2001

OTHER PUBLICATIONS

U.S. patent application Ser. No. 09/669,267, Ellison, filed Sep. 25, 2000.
U.S. patent application Ser. No. 09/669,997, Mutz et al., filed Sep. 25, 2000.
Elrod et al. (1989), "Nozzleless Droplet Formation with Focused Acoustic Beams," *J. Appl. Phys.* 65(9):3441–3447.
MacBeath et al. (2000), "Printing Proteins as Microarrays for High–Throughput Function Determination,"*Science* 289:1760–1763.
Theriault et al. (1999), "Application of Ink–jet Printing Technology to the Manufacture of Molecular Arrays," *DNA Microarrays, A Practical Approach*, Ed. M. Schena, Chapter 6 (Oxford University Press).

* cited by examiner

Primary Examiner—Maurie Garcia Baker
Assistant Examiner—Jon D. Epperson
(74) Attorney, Agent, or Firm—Dianne E. Reed; Reed & Eberle LLP

(57) ABSTRACT

The present invention provides a unique and highly accurate method for generating molecular arrays of very high density on porous surfaces. The method involves the application of focused acoustic energy to each of a plurality of fluid-containing reservoirs to eject a small fluid droplet—on the order of 1 picoliter or less—from each reservoir to a site on a porous substrate surface. High density molecular arrays are provided as well, in which greater than about 62,500 molecular moieties, serving as array elements, are present on a porous surface. Biomolecular arrays that can be generated using focused acoustic ejection include oligonucleotide arrays and peptidic arrays.

13 Claims, 3 Drawing Sheets

METHOD FOR GENERATING MOLECULAR ARRAYS ON POROUS SURFACES

CROSS-REFERENCE TO RELATED APPLICATIONS

This is a continuation-in-part of U.S. patent application Ser. No. 09/727,392, filed Nov. 29, 2000, abandoned, which is a continuation-in-part of U.S. patent application Ser. No. 09/669,996, filed Sep. 25, 2000, abandoned, the disclosures of which are incorporated by reference herein.

TECHNICAL FIELD

This invention relates generally to the use of focused acoustic energy in the preparation of molecular arrays, and more particularly relates to acoustic ejection of fluid droplets to prepare high density molecular arrays.

BACKGROUND

The discovery of novel materials having useful biological, chemical and/or physical properties often leads to emergence of useful products and technologies. Extensive research in recent years has focused on the development and implementation of new methods and systems for evaluating potentially useful chemical compounds. In the biomacromolecule arena, for example, much recent research has been devoted to potential methods for rapidly and accurately identifying the properties of various oligomers of specific monomer sequences, including ligand and receptor interactions, by screening high density arrays of biopolymers including nucleotidic, peptidic and saccharidic polymers.

For biological molecules, the complexity and variability of biological interactions and the physical interactions that determine, for example, protein conformation or structure other than primary structure, preclude predictability of biological, material, physical and/or chemical properties from theoretical considerations at this time. For non-biological materials, including bulk liquids and solids, despite much inquiry and vast advances in understanding, a theoretical framework permitting sufficiently accurate prediction de novo of composition, structure and synthetic preparation of novel materials is still lacking.

Consequently, the discovery of novel useful materials depends largely on the capacity to make and characterize new compositions of matter. Of the elements in the periodic table that can be used to make multi-elemental compounds, relatively few of the practically inexhaustible possible compounds have been made or characterized. A general need in the art consequently exists for a more systematic, efficient and economical method for synthesizing novel materials and screening them for useful properties. Further, a need exists for a flexible method to make compositions of matter of various material types and combinations of material types, including molecular materials, crystalline covalent and ionic materials, alloys, and combinations thereof such as crystalline ionic and alloy mixtures, or crystalline ionic and alloy layered materials.

The immune system is an example of systematic protein and nucleic acid macromolecular combinatorial chemistry that is performed in nature. Both the humoral and cell-mediated immune systems produce molecules having novel functions by generating vast libraries of molecules that are systematically screened for a desired property. For example, the humoral immune system is capable of determining which of $10^{12}$ B-lymphocyte clones that make different antibody molecules bind to a specific epitope or immunogenic locale, in order to find those clones that specifically bind various epitopes of an immunogen and stimulate their proliferation and maturation into plasma cells that make the antibodies. Because T cells, responsible for cell-mediated immunity, include regulatory classes of cells and killer T cells, and the regulatory T cell classes are also involved in controlling both the humoral and cellular response, more clones of T cells exist than of B cells, and must be screened and selected for appropriate immune response. Moreover, the embryological development of both T and B cells is a systematic and essentially combinatorial DNA splicing process for both heavy and light chains. See, e.g., *Therapeutic Immunology*, Eds. Austen et al. (Blackwell Science, Cambridge Mass., 1996).

Recently, the combinatorial prowess of the immune system has been harnessed to select for antibodies against small organic molecules such as haptens; some of these antibodies have been shown to have catalytic activity akin to enzymatic activity with the small organic molecules as substrate, termed "catalytic antibodies" (Hsieh et al. (1993) *Science* 260(5106):337–9). The proposed mechanism of catalytic antibodies is a distortion of the molecular conformation of the substrate towards the transition state for the reaction and additionally involves electrostatic stabilization. Synthesizing and screening large libraries of molecules has, not unexpectedly, also been employed for drug discovery. Proteins are known to form an induced fit for a bound molecule such as a substrate or ligand (Stryer, *Biochemistry*, 4th Ed. (1999) W. H. Freeman & Co., New York), with the bound molecule fitting into the site much like a hand fits into a glove, requiring some basic structure for the glove that is then shaped into the bound structure with the help of a substrate or ligand.

Geysen et al. (1987) *J Immun. Meth.* 102:259–274 have developed a combinatorial peptide synthesis in parallel on rods or pins involving functionalizing the ends of polymeric rods to potentiate covalent attachment of a first amino acid, and sequentially immersing the ends in solutions of individual amino acids. In addition to the Geysen et al. method, techniques have recently been introduced for synthesizing large arrays of different peptides and other polymers on solid surfaces. Arrays may be readily appreciated as additionally being efficient screening tools. Miniaturization of arrays saves synthetic reagents and conserves sample, a useful improvement in both biological and non-biological contexts. See, for example, U.S. Pat. Nos. 5,700,637 and 6,054,270 to Southern et al., which describe a method for chemically synthesizing a high density array of oligonucleotides of chosen monomeric unit length within discrete cells or regions of a support material, wherein the method employs an inkjet printer to deposit individual monomers on the support. So far, however, miniaturized arrays have been costly to make and contain significant amounts of undesired products at sites where a desired product is made. Thus, even in the biological arena, where a given sample might be unique and therefore priceless, use of high density biomacromolecule microarrays has met resistance by the academic community as being too costly, as yet insufficiently reliable compared to arrays made by lab personnel.

Arrays of thousands or even millions of different compositions of the elements may be formed by such methods. Various solid phase microelectronic fabrication derived polymer synthetic techniques have been termed "Very Large Scale Immobilized Polymer Synthesis," or "VLSIPS" technology. Such methods have been successful in screening potential peptide and oligonucleotide ligands for determining relative binding affinity of the ligand for receptors.

The solid phase parallel, spatially directed synthetic techniques currently used to prepare combinatorial biomolecule libraries require stepwise, or sequential, coupling of monomers. U.S. Pat. No. 5,143,854 to Pirrung et al. describes synthesis of polypeptide arrays, and U.S. Pat. No. 5,744,305 to Fodor et al. describes an analogous method of synthesizing oligo- and poly-nucleotides in situ on a substrate by covalently bonding photoremovable groups to the surface of the substrate. Selected substrate surface locales are exposed to light to activate them, by use of a mask. An amino acid or nucleotide monomer with a photoremovable group is then attached to the activated region. The steps of activation and attachment are repeated to make polynucleotides and polypeptides of desired length and sequence. Other synthetic techniques, exemplified by U.S. Pat. Nos. 5,700,637 and 6,054,270 to Southern et al., teach the use of inkjet printers, which are also substantially parallel synthesis because the synthetic pattern must be predefined prior to beginning to "print" the pattern. These solid phase synthesis techniques, which involve the sequential coupling of building blocks (e.g., amino acids) to form the compounds of interest, cannot readily be used to prepare many inorganic and organic compounds.

U.S. Pat. No. 5,985,356 to Schultz et al. teaches combinatorial chemistry techniques in the field of materials science, providing methods and a device for synthesis and use of an array of diverse materials in predefined regions of a substrate. An array of different materials on a substrate is prepared by delivering components of various compositions of matter to predefined substrate surface locales. This synthetic technique permits many classes of materials to be made by systematic combinatorial methods. Examples of the types of materials include, but are not limited to, inorganic materials, including ionic and covalent crystalline materials, intermetallic materials, metal alloys and composite materials including ceramics. Such materials can be screened for useful bulk and surface properties as the synthesized array, for example, electrical properties, including super- and semi-conductivity, and thermal, mechanical, thermoelectric, optical, optoelectronic, fluorescent and/or biological properties, including immunogenicity.

Discovery and characterization of materials often requires combinatorial deposition onto substrates of thin films of precisely known chemical composition, concentration, stoichiometry, area and/or thickness. Devices and methods for making arrays of different materials, each with differing composition, concentration, stoichiometry and thin-layer thickness at known substrate locales, permitting systematic combinatorial array based synthesis and analysis that utilize thin layer deposition methods, are already known. Although existing thin-layer methods have effected the precision of reagent delivery required to make arrays of different materials, the predefinition required in these synthetic techniques is inflexible, and the techniques are slow and thus relatively costly. Additionally, thin-layer techniques are inherently less suited to creating experimental materials under conditions that deviate drastically from conditions that are thermodynamically reversible or nearly so. Thus, a need exists for more efficient and rapid delivery of precise amounts of reagents needed for materials array preparation, with more flexibility as to predetermination and conditions of formation than attainable by thin-layer methods.

In combinatorial synthesis of biomacromolecules, U.S. Pat. Nos. 5,700,637 and 6,054,270 to Southern et al., as noted previously, describe a method for generating an array of oligonucleotides of chosen monomeric unit length within discrete cells or regions of a support material. The in situ method generally described for oligo- or polynucleotide synthesis involves: coupling a nucleotide precursor to a discrete predetermined set of cell locations or regions; coupling a nucleotide precursor to a second set of cell locations or regions; coupling a nucleotide precursor to a third set of cell locations or regions; and continuing the sequence of coupling steps until the desired array has been generated.

Covalent linking is effected at each location either to the surface of the support or to a nucleotide coupled in a previous step.

The patent '637 and patent '270 also teach that impermeable substrates are preferable to permeable substrates, such as paper, for effecting high combinatorial site densities, because the fluid volumes required will result in migration or wicking through a permeable substrate, precluding attainment of the small feature sizes required for high densities (such as those that are attainable by parallel photolithographic synthesis, which requires a substrate that is optically smooth and generally also impermeable; see U.S. Pat. No. 5,744,305 to Fodor et al.). As the inkjet printing method is a parallel synthesis technique that requires the array to be "predetermined" in nature, and therefore inflexible, and does not enable feature sites in the micron range or smaller, there remains a need in the art for a non-photolithographic in situ combinatorial array preparation method that can provide the high densities attainable by photolithographic arrays, a feat that requires small volumes of reagents and a highly accurate deposition method, without the inflexibility of a highly parallel process that requires a predetermined site sequence. Also, as permeable substrates offer a greater surface area for localization of array constituents, a method of effecting combinatorial high density arrays non-photolithographically by delivery of sufficiently small volumes to permit use of permeable substrates is also an advance over the current state of the art of array making.

As explained above, the parallel photolithographic in situ formation of biomolecular arrays of high density, e.g., oligonucleotide or polynucleotide arrays, is also known in the art. For example, U.S. Pat. Nos. 5,744,305 and 5,445,934 to Fodor et al. describe arrays of oligonucleotides and polynucleotides attached to a surface of a planar non-porous solid support at a density exceeding 400 and 1000 different oligonucleotides/cm$^2$ respectively. The arrays are generated using light-directed, spatially addressable synthesis techniques (see also U.S. Pat. Nos. 5,143,854 and 5,405,783, and International Patent Publication No. WO 90/15070). With respect to these photolithographic parallel in situ synthesized microarrays, Fodor et al. have developed photolabile nucleoside and peptide protecting groups, and masking and automation techniques; see U.S. Pat. No. 5,489,678 and International Patent Publication No. WO 92/10092).

The aforementioned patents disclose that photolithographic techniques commonly used in semiconductor fabrication may be applied in the fabrication of arrays of high density. Photolithographic in situ synthesis is best for parallel synthesis, requiring an inordinate number of masking steps to effect a sequential in situ combinatorial array synthesis. Even the parallel combinatorial array synthesis employing a minimized number of masking steps employs a significant number of such steps, which increases for each monomeric unit added in the synthesis. Further, the parallel photolithographic in situ array synthesis is inflexible and requires a predetermined mask sequence.

Because photolithographic fabrication requires a large number of masking steps, the yield for this process is lowered relative to a non-photolithographic in situ synthesis by the failure to block and/or inappropriate photo-deblocking by some of the photolabile protective groups. These problems with photolabile protective groups compound the practical yield problem for multi-step in situ syntheses in general by adding photochemical steps to the synthetic process. The problems have not been addressed by the advances made in the art of making and using such photolabile blockers for in situ synthesis, in part because some photolabile blocking groups are shielded from the light or "buried" by the polymer on which they reside, an effect exacerbated with increasing polymer length. Therefore, the purity of the desired product is low, as the array will contain significant impurities of undesired products that can reduce both sensitivity and selectivity.

As the photolithographic process for in situ synthesis defines site edges with mask lines, mask imperfections and misalignment, diffractive effects and perturbations of the optical smoothness of the substrate can combine to reduce purity by generating polymers similar in sequence and/or structure to the desired polymer as impurities, a problem that becomes more pronounced at the site edges. This is exacerbated when photolithographic protocols attempt to maximize site density by creating arrays that have abutting sites. Because the likelihood of a mask imperfection or misalignment increases with the number of masking steps and the associated number of masks, these edge effects are worsened by an increased number of masking steps and utilization of more mask patterns to fabricate a particular array. Site impurity, i.e., generation of polymers similar in sequence and/or structure to the desired polymer, leads to reduced sensitivity and selectivity for arrays designed to analyze a nucleotide sequence.

Some efforts have been directed to adapting printing technologies, particularly, inkjet printing technologies, to form biomolecular arrays. For example, U.S. Pat. No. 6,015,880 to Baldeschwieler et al. is directed to array preparation using a multistep in situ synthesis. A liquid microdrop containing a first reagent is applied by a single jet of a multiple jet reagent dispenser to a locus on the surface chemically prepared to permit covalent attachment of the reagent. The reagent dispenser is then displaced relative to the surface, or the surface is displaced with respect to the dispenser, and at least one microdrop containing either the first reagent or a second reagent from another dispenser jet is applied to a second substrate locale, which is also chemically activated to be reactive for covalent attachment of the second reagent. Optionally, the second step is repeated using either the first or second reagents, or different liquid-borne reagents from different dispenser jets, wherein each reagent covalently attaches to the substrate surface. The patent discloses that inkjet technology may be used to apply the microdrops.

Ordinary inkjet technology, however, suffers from a number of drawbacks. Often, inkjet technology involves heating or using a piezoelectric element to force a fluid through a nozzle in order to direct the ejected fluid onto a surface. Thus, the fluid may be exposed to a surface exceeding 200° C. before being ejected, and most, if not all, peptidic molecules, including proteins, degrade under such extreme temperatures. In addition, forcing peptidic molecules through nozzles creates shear forces that can alter molecular structure. Nozzles are subject to clogging, especially when used to eject a macromolecule-containing fluid, and the use of elevated temperatures exacerbates the problem because liquid evaporation results in deposition of precipitated solids on the nozzles. Clogged nozzles, in turn, can result in misdirected fluid or ejection of improperly sized droplets. Finally, ordinary inkjet technology employing a nozzle for fluid ejection generally cannot be used to deposit arrays with feature densities comparable to those obtainable using photolithography or other techniques commonly used in semiconductor processing.

A number of patents have described the use of acoustic energy in printing. For example, U.S. Pat. No. 4,308,547 to Lovelady et al. describes a liquid drop emitter that utilizes acoustic principles in ejecting droplets from a body of liquid onto a moving document to form characters or bar codes thereon. A nozzleless inkjet printing apparatus is used wherein controlled drops of ink are propelled by an acoustical force produced by a curved transducer at or below the surface of the ink. In contrast to inkjet printing devices, nozzleless fluid ejection devices described in the aforementioned patent are not subject to clogging and the disadvantages associated therewith, e.g., misdirected fluid or improperly sized droplets.

The applicability of nozzleless fluid ejection has generally been appreciated for ink printing applications. Development of ink printing applications is primarily economically driven by printing cost and speed for acceptable text. For acoustic printing, development efforts have therefore focused on reducing printing costs rather than improving quality, and on increasing printing speed rather than accuracy. For example, U.S. Pat. No. 5,087,931 to Rawson is directed to a system for transporting ink under constant flow to an acoustic ink printer having a plurality of ejectors aligned along an axis, each ejector associated with a free surface of liquid ink. When a plurality of ejectors is used instead of a single ejector, printing speed generally increases, but controlling fluid ejection, specifically droplet placement, becomes more difficult.

U.S. Pat. No. 4,797,693 to Quate describes an acoustic ink printer for printing polychromatic images on a recording medium. The printer is described as comprising a combination of a carrier containing a plurality of differently colored liquid inks, a single acoustic printhead acoustically coupled to the carrier for launching converging acoustic waves into the carrier, an ink transport means to position the carrier to sequentially align the differently colored inks with the printhead, and a controller to modulate the radiation pressure used to eject ink droplets. This printer is described as designed for the realization of cost savings. Because two droplets of primary color, e.g., cyan and yellow, deposited in sufficient proximity will appear as a composite or secondary color, the level of accuracy required is fairly low and inadequate for biomolecular array formation. Such a printer is particularly unsuitable for in situ synthesis requiring precise droplet deposition and consistent placement, so that the proper chemical reactions occur. That is, the drop placement accuracy needed to effect perception of a composite secondary color is much lower than is required for chemical synthesis at photolithographic density levels. Consequently, an acoustic printing device that is suitable for printing visually ascertainable material is inadequate for microarray preparation. Also, this device can eject only a limited quantity of ink from the carrier before the liquid meniscus moves out of acoustic focus and drop ejection ceases. This is a significant limitation with biological fluids, which are typically far more costly and rare than ink. The Quate et al. patent does not address how to use most of the fluid in a closed reservoir without adding additional liquid from an external source.

Thus, there is a general need in the art for improved array preparation methodology. An ideal array preparation technique would provide for highly accurate deposition of minute volumes of fluids on a substrate surface, wherein droplet volume—and thus "spot" size on the substrate surface—can be carefully controlled and droplets can be precisely directed to particular sites on a substrate surface. It would also be optimal if such a technique could be used with porous or even permeable surfaces, as such surfaces can provide substantially greater surface area on which to attach molecular moieties that serve as array elements, and would enable preparation of higher density arrays. To date, as alluded to above, high density arrays have been prepared only on nonporous, impermeable surfaces, and only low density arrays could be prepared on porous surfaces.

SUMMARY OF THE INVENTION

Accordingly, it is an object of the present invention to provide methods and molecular arrays that address the aforementioned need in the art. It has now been discovered that focused acoustic energy can be advantageously used with very small fluid volumes, on the order of 1 picoliter or less, to prepare high density arrays on substrates having a porous or even a permeable surface. Prior array fabrication methods have not enabled preparation of high density arrays on porous or permeable surfaces because prior spotting processes are nowhere near as accurate as the present acoustic deposition method, and prior processes have also required larger droplet volumes. In contrast to prior methods of manufacturing arrays, then, the present acoustic ejection process enables highly accurate deposition of extremely small liquid droplets, such that diffusion of a deposited droplet into neighboring cells is not a problem, and ultra-high array densities can now be achieved with high porosity, permeable surfaces. Porous, permeable surfaces can provide substantially more surface area on which to attach molecules within an array, as the biomolecules can penetrate the surface of the substrate and can thus generate a substantially larger signal per unit of projected area due to the resulting non-planar distribution of the molecules on and within the substrate surface.

The present invention overcomes a significant disadvantage of the prior art, since prior methods could not constrain the formation or deposition of biomolecules to a small region, due to the inability to localize the synthesis process or to restrict the migration of materials to prevent adjacent "spots" from diffusing into each other. The accurate placement of extremely small volumes of fluids can enable both multistep in situ synthesis on a substrate surface and deposition of an intact molecule within an extraordinarily small zone without the need to mask, pre-activate surface sites, or otherwise modify a predetermined region of a surface.

The invention makes use of a focused acoustic energy device as described in U.S. patent application Ser. No. U09/669,996 ("Acoustic Ejection of Fluids from a Plurality of Reservoirs"), inventors Ellson, Foote and Mutz, filed on Sep. 25, 2000, and assigned to Picoliter, Inc. (Sunnyvale, Calif.). As described in the aforementioned patent application, the device enables acoustic ejection of a plurality of fluid droplets toward designated sites on a substrate surface for deposition thereon, and comprises: a plurality of reservoirs or other fluid-containing means, each adapted to contain a fluid; an acoustic ejector that includes an acoustic radiation generator and a focusing means for focusing the generated acoustic radiation at a focal point sufficiently near the fluid surface in each of the reservoirs such that droplets are ejected therefrom; and a means for positioning the ejector in acoustic coupling relationship to each of the reservoirs. Preferably, each of the reservoirs is removable, comprised of an individual well in a well plate, and/or arranged in an array. In addition, it is preferred that the reservoirs are substantially acoustically indistinguishable from one another.

Focused acoustic ejection is carried out by positioning the acoustic ejector so as to be in acoustically coupled relationship with a first fluid-containing reservoir, and then activating the ejector to generate and direct acoustic radiation into the fluid so as to eject a fluid droplet toward a site on a porous substrate surface. Then, the ejector is repositioned so as to be in acoustically coupled relationship with a second fluid-containing reservoir and activated again as above to eject a droplet of the second fluid toward a second site on the porous surface. The method may be repeated with a plurality of fluid reservoirs each containing a fluid, with each reservoir generally although not necessarily containing a different fluid. The acoustic ejector is thus repeatedly repositioned so as to eject a droplet from each reservoir toward a different site on a substrate surface, or toward sites that already have a droplet "spot" thereon. In such a way, the method is readily adapted for use in generating an array of molecular moieties on a porous surface.

The invention also provides high density arrays of various molecular moieties, typically biomolecules, on a porous substrate surface. The arrays provided by the instant invention do not possess the edge effects that result from optical and alignment effects of photolithographic masking, nor are they subject to imperfect spotting alignment from inkjet nozzle-directed deposition of reagents. Focused acoustic ejection can be used to prepare molecular arrays on porous surfaces that have a density of greater than about 62,500 molecular moieties, or array elements, per square centimeter of substrate surface, preferably a density of greater than about 250,000, more preferably greater than about 1,000,000, still more preferably greater than about 1,500,000, and most preferably in the range of about 1,500,000 to about 4,000,000 molecular moieties per square centimeter of substrate surface.

BRIEF DESCRIPTION OF THE DRAWINGS

FIG. 1A shows the acoustic ejector acoustically coupled to the first reservoir and having been activated in order to eject a droplet of fluid from within the first reservoir toward a site on a substrate surface. FIG. 1B shows the acoustic ejector acoustically coupled to a second reservoir.

FIG. 2A illustrates the ejection of a droplet of surface modification fluid onto a site of a substrate surface. FIG. 2B illustrates the ejection of a droplet of a first fluid containing a first molecular moiety adapted for attachment to the modified surface of the substrate. FIG. 2C illustrates the ejection of a droplet of second fluid containing a second molecular moiety adapted for attachment to the first molecule. FIG. 2D illustrates the substrate and the dimer synthesized in situ by the process illustrated in FIGS. 2A, 2B and 2C.

DETAILED DESCRIPTION OF THE INVENTION

Figure 1A:
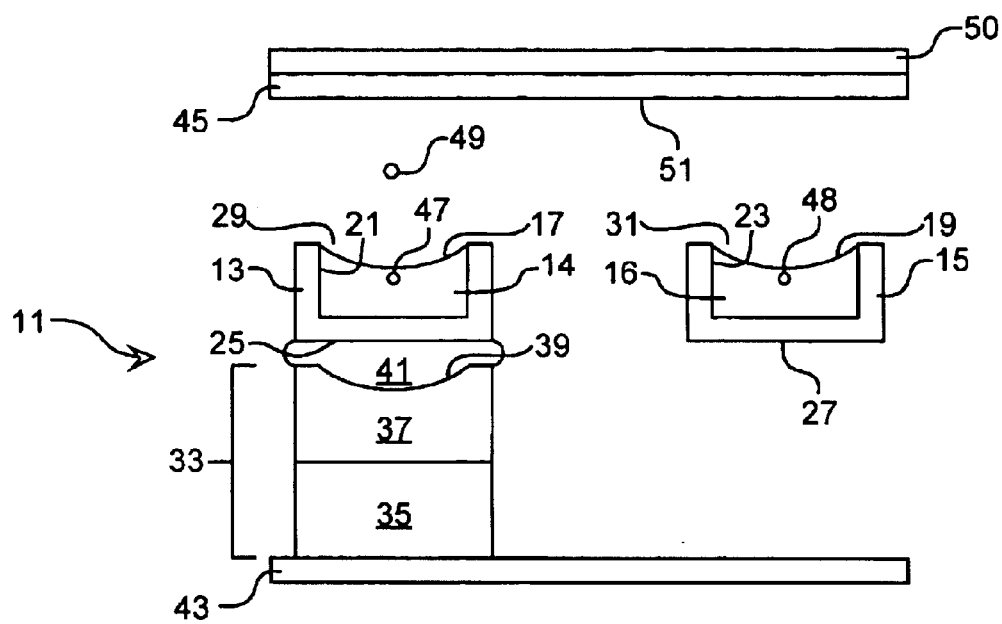
FIGS. 1A and 1B, collectively referred to as FIG. 1, schematically illustrate in simplified cross-sectional view an embodiment of the inventive device comprising first and second reservoirs, an acoustic ejector, and an ejector positioning means.

Before describing the present invention in detail, it is to be understood that this invention is not limited to specific fluids, biomolecules or device structures, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a reservoir" includes a plurality of reservoirs, reference to "a fluid" includes a plurality of fluids, reference to "a biomolecule" includes a combination of biomolecules, and the like.

In describing and claiming the present invention, the following terminology will be used in accordance with the definitions set out below.

The terms "acoustic coupling" and "acoustically coupled" used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "adsorb" as used herein refers to the noncovalent retention of a molecule by a substrate surface. That is, adsorption occurs as a result of noncovalent interaction between a substrate surface and adsorbing moieties present on the molecule that is adsorbed. Adsorption may occur through hydrogen bonding, van der Waal's forces, polar attraction or electrostatic forces (i.e., through ionic bonding). Examples of adsorbing moieties include, but are not limited to, amine groups, carboxylic acid moieties, hydroxyl groups, nitroso groups, sulfones and the like. Often the substrate may be functionalized with adsorbent moieties to interact in a certain manner, as when the surface is functionalized with amino groups to render it positively charged in a pH neutral aqueous environment. Likewise, adsorbate moieties may be added in some cases to effect adsorption, as when a basic protein is fused with an acidic peptide sequence to render adsorbate moieties that can interact electrostatically with a positively charged adsorbent moiety.

The term "attached," as in, for example, a substrate surface having a moiety "attached" thereto, includes covalent binding, adsorption, and physical immobilization. The terms "binding" and "bound" are identical in meaning to the term "attached."

The term "array" used herein refers to a two-dimensional arrangement of features such as an arrangement of reservoirs (e.g., wells in a well plate) or an arrangement of different materials including ionic, metallic or covalent crystalline, including molecular crystalline, composite or ceramic, glassine, amorphous, fluidic or molecular materials on a substrate surface (as in an oligonucleotide or peptidic array). Different materials in the context of molecular materials includes chemical isomers, including constitutional, geometric and stereoisomers, and in the context of polymeric molecules constitutional isomers having different monomer sequences. Arrays are generally comprised of regular, ordered features, as in, for example, a rectilinear grid, parallel stripes, spirals, and the like, but non-ordered arrays may be advantageously used as well. The arrays or patterns formed using the devices and methods of the invention generally have no optical significance to the unaided human eye. For example, the invention does not involve ink printing on paper or other substrates in order to form letters, numbers, bar codes, figures, or other inscriptions that have optical significance to the unaided human eye. In addition, arrays and patterns formed by the deposition of ejected droplets on a porous surface as provided herein are preferably substantially invisible to the unaided human eye.

The terms "biomolecule" and "biological molecule" are used interchangeably herein to refer to any organic molecule, whether naturally occurring, recombinantly produced, or chemically synthesized in whole or in part, that is, was or can be a part of a living organism. The terms encompass, for example, nucleotides, amino acids and monosaccharides, as well as oligomeric and polymeric species such as oligonucleotides and polynucleotides, peptidic molecules such as oligopeptides, polypeptides and proteins, saccharides such as disaccharides, oligosaccharides, polysaccharides, mucopolysaccharides or peptidoglycans (peptido-polysaccharides) and the like. The term also encompasses ribosomes, enzyme cofactors, pharmacologically active agents, and the like.

The terms "library" and "combinatorial library" are used interchangeably herein to refer to a plurality of chemical or biological moieties present on the surface of a substrate, wherein each moiety is different from each other moiety. The moieties may be, e.g., peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "oligonucleotide" shall be generic to polydeoxynucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones (for example PNAs), providing that the polymers contain nucleobases in a configuration that allows for base pairing and base stacking, such as is found in DNA and RNA. Thus, these terms include known types of oligonucleotide modifications, for example, substitution of one or more of the naturally occurring nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the term "polynucleotide" and "oligonucleotide," and these terms will be used interchangeably. These terms refer only to the primary structure of the molecule. As used herein the symbols for nucleotides and polynucleotides are according to the IUPAC-IUB Commission of Biochemical Nomenclature recommendations (*Biochemistry* 9:4022, 1970).

The terms "peptide," "peptidyl" and "peptidic" as used throughout the specification and claims are intended to include any structure comprised of two or more amino acids. For the most part, the peptides in the present arrays comprise about 5 to 10,000 amino acids, preferably about 5 to 1000 amino acids. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptidic molecules forming the present arrays may be replaced by a non-conventional amino acid. In general, conservative replacements are preferred. Conservative replacements substitute the original amino acid with a non-conventional amino acid that resembles the original in one or more of its characteristic properties (e.g., charge, hydrophobicity, stearic bulk; for example, one may replace Val with Nval). The term "non-conventional amino acid" refers to amino acids other than conventional amino acids, and include, for example, isomers and modifications of the conventional amino acids (e.g., D-amino acids), non-protein amino acids, post-translationally modified amino acids, enzymatically modified amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and nor-leucine), and peptides having the naturally occurring amide —CONH— linkage replaced at one or more sites within the peptide backbone with a non-conventional linkage such as N-substituted amide, ester, thioamide, retropeptide (—NHCO—), retrothioamide (—NHCS—), sulfonamido (—SO$_2$NH—), and/or peptoid (N-substituted glycine) linkages. Accordingly, the peptidic molecules of the array include pseudopeptides and peptidomimetics. The peptides of this invention can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

Peptidic compounds include any pharmacologically active peptide, polypeptide or protein, such as, but not limited to enzymes, monoclonal and polyclonal antibodies, antigens, coagulation modulators, cytokines, endorphins, peptidyl hormones, kinins, and structurally similar bioactive equivalents thereof. By a "structurally similar bioactive equivalent" is meant a peptidyl compound with structure sufficiently similar to that of an identified bioactive peptidyl compound to produce substantially equivalent therapeutic effects. As used herein and in the appended claims, the terms "protein", "peptide" and "polypeptide" refer to both the specific peptidic compound(s) identified as well as structurally similar bioactive equivalents thereof.

Examples of various peptidyl compounds include, but are not limited to, the following:

coagulation modulators, such as $\alpha_1$-antitrypsin, $\alpha_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, thrombomodulin and combinations thereof;

cytokines, such as: transforming growth factors (TGFs), including TGF-β2, TGF-β2, and TGF-β3; bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), heparin-binding neurotrophic factor (HBNF), and insulin-like growth factor (IGF)); connective tissue activated peptides (CTAPs), osteogenic factors; colony stimulating factor; interferons, including interferon-α, interferon α-2a, interferon α-2b, interferon α-n3, interferon-β, and interferon-γ; interleukins, including interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, and interleukin-17; tumor necrosis factor; tumor necrosis factor-α; granuloycte colony-stimulating factor (G-CSF); granulocyte-macrophage colony-stimulating factor (GM-CSF); macrophage colony-stimulating factor; Inhibins (e.g., Inhibin A and Inhibin B); growth differentiating factors (e.g., GDF-1); Activins (e.g., Activin A, Activin B, and Activin AB); midkine (MD); and thymopoietin.

endorphins, i.e., peptides that activate opiate receptors, including pharmacologically active endorphin derivatives such as dermorphin, dynorphin, α-endorphin, β-endorphin, γ-endorphin, σ-endorphin [Leu$^5$] enkephalin, [Met$^5$]enkephalin, substance P, and combinations thereof;

peptidyl hormones, such as activin, amylin, angiotensin, atrial natriuretic peptide (ANP), calcitonin (derived from chicken, eel, human, pig, rat, salmon, etc.), calcitonin gene-related peptide, calcitonin N-terminal flanking peptide, cholecystokinin (CCK), ciliary neurotrophic factor (CNTF), corticotropin (adrenocorticotropin hormone, ACTH), corticotropin-releasing factor (CRF or CRH), follicle-stimulating hormone (FSH), gastrin, gastrin inhibitory peptide (GIP), gastrin-releasing peptide, glucagon, gonadotropin-releasing factor (GnRF or GNRH), growth hormone releasing factor (GRF, GRH), human chorionic gonadotropin (hCH), inhibin A, inhibin B, insulin (derived from beef, human, pig, etc.), leptin, lipotropin (LPH), luteinizing hormone (LH), luteinizing hormone-releasing hormone (LHRH), lypressin, α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatostatin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, triiodothyronine, vasoactive intestinal peptide (VIP), and vasopressin (antidiuretic hormone, ADH);

analogues of LHRH, such as buserelin, deslorelin, fertirelin, goserelin, histrelin, leuprolide (leuprorelin), lutrelin, nafarelin, tryptorelin and combinations thereof;

kinins, such as bradykinin, potentiator B, bradykinin potentiator C, and kallidin and combinations thereof.

enzymes, such as transferases, hydrolases, isomerases, proteases, ligases and oxidoreductases such as esterases, phosphatases, glycosidases and peptidases. Specific examples of enzymes include super oxide dismutase (SOD), tissue plasminogen activator (TPA), renin, adenosine deaminase, β-glucocerebrosidase, asparaginase, dornase-α, hyaluronidase, elastase, trypsin, thymidin kinase (TK), tryptophan hydroxylase, urokinase, and kallikrein;

enzyme inhibitors, such as leupeptin, chymostatin, pepslatin, renin inhibitors, angiotensin converting enzyme (ACE) inhibitors, and the like;

antibodies, including both monoclonal and polyclonal antibodies, as well as antibody fragments, such as the F(ab')$_2$, Fab, Fv and Fc fragments of monoclonal antibodies; and other peptidyl drugs, such as abarelix, anakinra, ancestim, bivalirudin, bleomycin, bombesin, desmopressin acetate, des-Q14-ghrelin, enterostatin, erythropoeitin, exendin-4, filgrastim, gonadorelin, insulinotropin, lepirudin, magainin I, magainin II, nerve growth factor, pentigetide, thrombopoietin, thymosin α-1, and urotensin II and combinations thereof.

The term "fluid" as used herein refers to matter that is nonsolid or at least partially gaseous and/or liquid. A fluid may contain a solid that is minimally, partially or fully solvated, dispersed or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

The term "near" is used to refer to the distance from the focal point of the focused acoustic radiation to the surface of the fluid from which a droplet is to be ejected. The distance should be such that the focused acoustic radiation directed into the fluid results in droplet ejection from the fluid surface, and one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the 1997 IS&T NIP13 International Conference on Digital Printing Technologies Proceedings*, at pp. 698–702.

The term "reservoir" as used herein refers to a receptacle or chamber for holding or containing a fluid. Thus, a fluid in a reservoir necessarily has a free surface, i.e., a surface that allows a droplet to be ejected therefrom. A reservoir may also be a locus on a substrate surface within which a fluid is constrained.

The term "substrate" as used herein refers to a substrate having a porous surface. The entire substrate may be porous, in which case the porous surface is the surface of the substrate itself. Alternatively, a nonporous substrate may be used providing that a porous surface layer is present that provides the porous surface. The substrate may be constructed in any of a number of forms such as wafers, slides, well plates, membranes, etc. Suitable substrates include uncoated porous glass slides, including controlled pore glass (CPG) slides; porous glass slides coated with a polymeric coating, e.g., an aminosilane or poly-L-lysine coating, thus having a porous polymeric surface; and nonporous glass slides coated with a porous coating, such as may be comprised of a cellulosic polymer (e.g., nitrocellulose), polyacrylamide, or a porous metal (for example, comprised of microporous aluminum). Examples of commercially available substrates having porous surfaces include the Fluorescent Array Surface Technology (FAST™) slides available from Schleicher & Schuell, Inc. (Keene, N. H.), which are coated with a 10–30 μm thick porous, fluid-permeable nitrocellulose layer that substantially increases the available binding area per unit area of surface. Other commercially available porous substrates include the CREATIVECHIP® permeable slides currently available from Eppendorf AG (Hamburg, Germany), and substrates having "three-dimensional" geometry, by virtue of an ordered, highly porous structure that enables reagents to flow into and penetrate through the pores and channels of the entire structure. Such substrates are available from Gene Logic, Inc. under the tradename "Flow-Thru Chip," and are described by Steel et al. in Chapter 5 of *Microarray Biochip Technology* (BioTechniques Books, Natick, Mass., 2000).

The term "porous" as in a "porous substrate" or a "substrate having a porous surface," refers to a substrate or surface, respectively, having a porosity (void percentage) in the range of about 1% to about 99%, preferably about 5% to about 99%, more preferably in the range of about 15% to about 95%, and an average pore size of about 100 Å to about 1 mm, typically about 500 Å to about 0.5 mm.

The term "impermeable" is used in the conventional sense to mean not permitting water or other fluid to pass through. The term "permeable" as used herein means not "impermeable." Thus, a "permeable substrate" and a "substrate having a permeable surface" refer to a substrate or surface, respectively, which can be permeated with water or other fluid.

While the foregoing support materials are representative of conventionally used substrates, it is to be understood that a substrate may in fact comprise any biological, nonbiological, organic and/or inorganic material so long as a porous surface is provided, and may be in any of a variety of physical forms, e.g., particles, strands, precipitates, gels, sheets, tubing, spheres, containers, capillaries, pads, slices, films, plates, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionalities that covalently link a compound to the substrate surface. These are widely known and include, for example, silicon dioxide supports containing reactive Si—OH groups, polyacrylamide supports, polystyrene supports, polyethylene glycol supports, and the like.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

"Optional" or "optionally" means that the subsequently described circumstance may or may not occur, so that the description includes instances where the circumstance occurs and instances where it does not.

The term "substantially" as in, for example, the phrase "substantially all molecules of an array," refers to at least 90%, preferably at least 95%, more preferably at least 99%, and most preferably at least 99.9%, of the molecules of an array. Other uses of the term "substantially" involve an analogous definition.

The invention accordingly provides a method for acoustically generating fluid droplets from a plurality of individual reservoirs to form a high density molecular array on a porous substrate surface. That is, focused acoustic energy is used to eject single fluid droplets from the free surface of a fluid (e.g., in a reservoir or well plate), generally toward discrete sites on a porous substrate surface, enabling extraordinarily precise deposition and consistent droplet size and velocity. The device comprises a plurality of reservoirs, each adapted to contain a fluid, an ejector comprising an acoustic radiation generator for generating acoustic radiation and a focusing means for focusing the acoustic radiation generated (at a focal point within and sufficiently near the fluid surface in each of the reservoirs to result in the ejection of droplets therefrom), and a means for positioning the ejector in acoustic coupling relationship to each of the reservoirs.

The use of such a focused acoustic ejection system enables preparation of arrays on porous surfaces that will generally have a density in the range of at least 62,500 molecular moieties as array "elements" (e.g., surface-bound oligomers) per square centimeter of substrate surface, preferably at least 250,000 molecular moieties per square centimeter of substrate surface, more preferably at least 1,000,000, most preferably at least 1,500,000, and optimally in the range of about 1,500,000 to about 4,000,000 molecular moieties per square centimeter of substrate surface. Each molecular moiety may be different from every other molecular moiety within the array, such that the array is a "combinatorial" library of the different molecular moieties.

A significant advantage of using focused acoustic energy technology in the manufacture of arrays is that the aforementioned array densities may be achieved on substrates with porous surfaces, and even permeable surfaces. More specifically, the present acoustic ejection method can be used to manufacture high density arrays that can be read with a high precision digitizing scanner capable of 2 $\mu$m resolution, by depositing droplets having a volume on the order of 1 pL, resulting in deposited spots about 18 $\mu$m in diameter. For ultra-high density arrays, a smaller droplet volume is necessary, typically less than about 0.03 pL (deposition of droplets having a volume on the order of 0.025 pL will result in deposited spots about 4.5 $\mu$m in diameter). Localization of deposited droplets using chemical or physical means, such as described in 6,054,270 to Southern et al., is unnecessary because acoustic ejection enables precisely directed minute droplets to be deposited with extraordinary accuracy at a particular site.

FIG. 1 illustrates a focused acoustic ejection device in simplified cross-sectional view. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs, with a first reservoir indicated at 13 and a second reservoir indicated at 15, each adapted to contain a fluid having a fluid surface, e.g., a first fluid 14 and a second fluid 16 having fluid surfaces respectively indicated at 17 and 19. Fluids 14 and 16 may the same or different. As shown, the reservoirs are of substantially identical construction so as to be substantially acoustically indistinguishable, but identical construction is not a requirement. The reservoirs are shown as separate removable components but may, if desired, be fixed within a plate or other substrate. For example, the plurality of reservoirs may comprise individual wells in a well plate, optimally although not necessarily arranged in an array. Each of the reservoirs 13 and 15 is preferably axially symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33 comprised of an acoustic radiation generator 35 for generating acoustic radiation and a focusing means 37 for focusing the acoustic radiation at a focal point within the fluid from which a droplet is to be ejected, near the fluid surface. As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15 and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector.

As will be appreciated by those skilled in the art, any of a variety of focusing means may be employed in conjunction with the present invention. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane.

There are also a number of ways to acoustically couple the ejector 33 to each individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination. The cleaning process would necessarily lengthen the transition time between each droplet ejection event. In addition, in such a method, fluid would adhere to the ejector as it is removed from each container, wasting material that may be costly or rare.

Thus, a preferred approach would be to acoustically couple the ejector to the reservoirs and reservoir fluids without contacting any portion of the ejector, e.g., the focusing means, with any of the fluids to be ejected. To this end, the present invention provides an ejector positioning means for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and each of the reservoirs through indirect contact, as illustrated in FIG. 1A. In the figure, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave is generated by the acoustic radiation generator and directed by the focusing means 37 into the acoustic coupling medium 41, which then transmits the acoustic radiation into the reservoir 13.

In operation, reservoirs 13 and 15 of the device are each filled with first and second fluids 14 and 16, respectively, as shown in FIG. 1. The acoustic ejector 33 is positionable by means of ejector positioning means 43, shown below reservoir 13, in order to achieve acoustic coupling between the ejector and the reservoir through acoustic coupling medium 41. Substrate 45 is positioned above and in proximity to the first reservoir 13 such that one surface of the substrate, shown in FIG. 1 as underside surface 51, faces the reservoir and is substantially parallel to the surface 17 of the fluid 14 therein. Once the ejector, the reservoir and the substrate are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 onto a designated site on the underside surface 51 of the substrate. The ejected droplet may be retained on the substrate surface by solidifying thereon after contact; in such an embodiment, it is necessary to maintain the substrate at a low temperature, i.e., a temperature that results in droplet solidification after contact. Alternatively, or in addition, a molecular moiety within the droplet attaches to the substrate surface after contract, through adsorption, physical immobilization, or covalent binding.

Figure 1B:
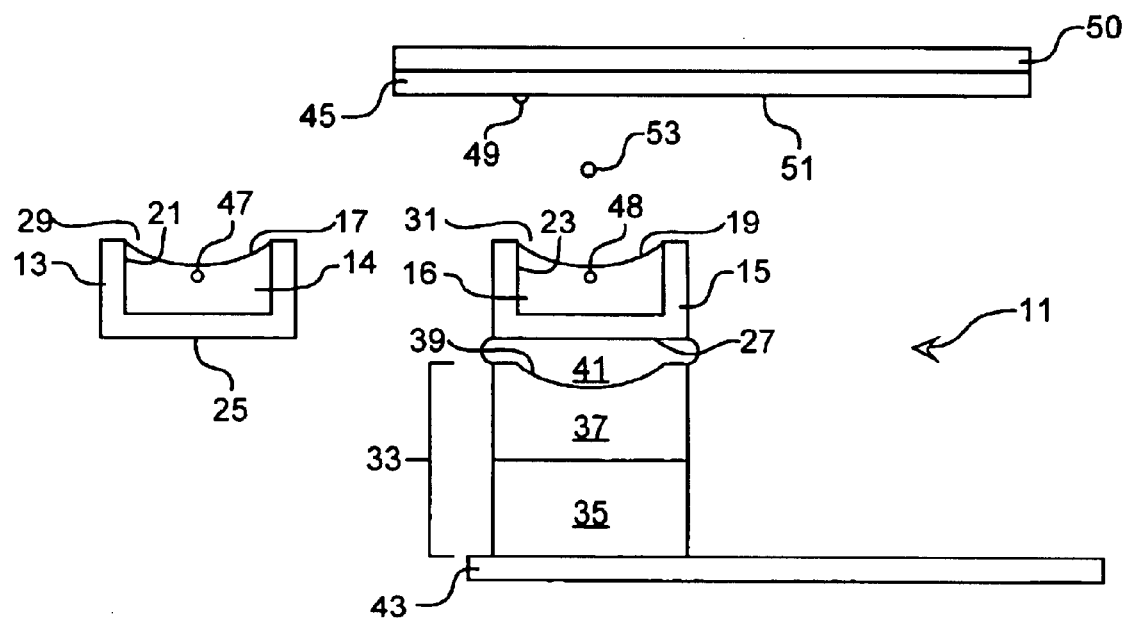

Then, as shown in FIG. 1B, a substrate positioning means 50 repositions the substrate 45 over reservoir 15 in order to receive a droplet therefrom at a second designated site. FIG. 1B also shows that the ejector 33 has been repositioned by the ejector positioning means 43 below reservoir 15 and in acoustically coupled relationship thereto by virtue of acoustic coupling medium 41. Once properly aligned as shown in FIG. 1B, the acoustic radiation generator 35 of ejector 33 is activated to produce acoustic radiation that is then directed by focusing means 37 to a focal point within fluid 16 near the fluid surface 19, thereby ejecting droplet 53 onto the substrate. It should be evident that such operation is illustrative of how the inventive device may be used to eject a plurality of fluids from reservoirs in order to form a pattern, e.g., an array, on the substrate surface 51. It should be similarly evident that the device may be adapted to eject a plurality of droplets from one or more reservoirs onto the same site of the substrate surface.

As discussed above, either individual, e.g., removable, reservoirs or well plates may be used to contain fluids that are to be ejected, wherein the reservoirs or the wells of the well plate are preferably substantially acoustically indistinguishable from one another. Also, unless it is intended that the ejector is to be submerged in the fluid to be ejected, the reservoirs or well plates must have acoustic transmission properties sufficient to allow acoustic radiation from the ejector to be conveyed to the surfaces of the fluids to be ejected. Typically, this involves providing reservoir or well bases that are sufficiently thin to allow acoustic radiation to travel therethrough without unacceptable dissipation. In addition, the material used in the construction of reservoirs must be compatible with the fluids contained therein. Thus, if it is intended that the reservoirs or wells contain an organic solvent such as acetonitrile, polymers that dissolve or swell in acetonitrile would be unsuitable for use in forming the reservoirs or well plates. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. Many well plates suitable for use with the employed device are commercially available and may contain, for example, 96, 384 or 1536 wells per well plate. Manufactures of suitable well plates for use in the employed device include Corning Inc. (Coming, N.Y.) and Greiner America, Inc. (Lake Mary, Fla.). However, the availability of such commercially available well plates does not preclude manufacture and use of custom-made well plates containing at least about 10,000 wells, or as many as 100,000 wells or more. For array forming applications, it is expected that about 100,000 to about 4,000,000 or more reservoirs may be employed. In addition, to reduce the amount of movement and time needed to align the ejector with each reservoir or reservoir well, it is preferable that the center of each reservoir is located not more than about 1 centimeter, preferably not more than about 1 millimeter and optimally not more than about 0.5 millimeter from a neighboring reservoir center.

Moreover, the present methodology may be adapted to eject fluids of virtually any type and amount desired. The fluid may be aqueous and/or nonaqueous. Examples of fluids include, but are not limited to, aqueous fluids such as water per se and water-solvated ionic and non-ionic solutions, organic solvents, and lipidic liquids, suspensions of immiscible fluids and suspensions or slurries of solids in liquids. Because the invention is readily adapted for use with high temperatures, fluids such as liquid metals, ceramic materials, and glasses may be used; see, e.g., co-pending patent application U.S. Ser. No. 09/669,194 ("Method and Apparatus for Generating Droplets of Immiscible Fluids"), inventors Ellson and Mutz, filed on Sep. 25, 2000, and assigned to Picoliter, Inc. (Sunnyvale, Calif.). U.S. Pat. Nos. 5,520,715 and 5,722,479 to Oeftering describe the use of acoustic ejection for liquid metal for forming structures using a single reservoir and adding fluid to maintain focus. U.S. Pat. No. 6,007,183 to Horine is another patent that pertains to the use of acoustic energy to eject droplets of liquid metal. The capability of producing fine droplets of such materials is in sharp contrast to piezoelectric technology, insofar as piezoelectric systems perform suboptimally at elevated temperatures. Furthermore, because of the precision that is possible using the inventive technology, the device may be used to eject droplets from a reservoir adapted to contain no more than about 100 nanoliters of fluid, preferably no more than 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules, wherein it may be desirable to eject droplets having a volume of about 1 picoliter or less, e.g., having a volume in the range of about 0.025 pL to about 1 pL.

It will be appreciated that various components of a suitable acoustic ejection device may require individual control or synchronization to form an array on a substrate. For example, the ejector positioning means may be adapted to eject droplets from each reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector and the activation of the ejector to ensure proper array formation.

The device may also include certain performance-enhancing features. For example, the device may include a cooling means for lowering the temperature of the substrate surface to ensure, for example, that the ejected droplets adhere to the substrate. The cooling means may be adapted to maintain the substrate surface at a temperature that allows fluid to partially or preferably substantially solidify after the fluid comes into contact therewith. In the case of aqueous fluids, the cooling means should have the capacity to maintain the substrate surface at about 0° C. In addition, repeated application of acoustic energy to a reservoir of fluid may result in heating of the fluid. Heating can of course result in unwanted changes in fluid properties such as viscosity, surface tension and density. Thus, the device may further comprise means for maintaining fluid in the reservoirs at a constant temperature. Design and construction of such temperature maintaining means are known to one of ordinary skill in the art and may comprise, e.g., components such a heating element, a cooling element, or a combination thereof. For many biomolecular deposition applications, it is generally desired that the fluid containing the biomolecule is kept at a constant temperature without deviating more than about 1° C. or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection.

For some applications, especially those involving acoustic deposition of molten metals or other materials, a heating element may be provided for maintaining the substrate at a temperature below the melting point of the molten material, but above ambient temperature so that control of the rapidity of cooling may be effected. The rapidity of cooling may thus be controlled, to permit experimentation regarding the properties of combinatorial compositions such as molten deposited alloys cooled at different temperatures. For example, it is known that metastable materials are generally more likely to be formed with rapid cooling, and other strongly irreversible conditions. The approach of generating materials by different cooling or quenching rates may be termed combinatorial quenching, and could be effected by changing the substrate temperature between acoustic ejections of the molten material. A more convenient method of evaluating combinatorial compositions solidified from the molten state at different rates is by generating multiple arrays having the same pattern of nominal compositions ejected acoustically in the molten state onto substrates maintained at different temperatures.

In some cases, a substrate surface may be modified prior to formation of an array thereon. Surface modification may involve functionalization or defunctionalization, smoothing or roughening, changing surface conductivity, coating, degradation, passivation or otherwise altering the surface's chemical composition or physical properties. A preferred surface modification method involves altering the wetting properties of the surface, for example to facilitate confinement of a droplet ejected on the surface within a designated area or enhancement of the kinetics for the surface attachment of molecular moieties contained in the ejected droplet. A preferred method for altering the wetting properties of the substrate surface involves deposition of droplets of a suitable surface modification fluid at each designated site of the substrate surface prior to acoustic ejection of fluids to form an array thereon. In this way, the "spread" of the acoustically ejected droplets may be optimized and consistency in spot size (i.e., diameter, height and overall shape) ensured. One way to implement the method involves acoustically coupling the ejector to a modifier reservoir containing a surface modification fluid and then activating the ejector, as described in detail above, to produce and eject a droplet of surface modification fluid toward a designated site on the substrate surface. The method is repeated as desired to deposit surface modification fluid at additional designated sites. This method is useful in a number of applications including, but not limited to, spotting oligomers to form an array on a substrate surface or synthesizing array oligomers in situ. As noted above, other physical properties of the surface that may be modified include thermal properties and electrical conductivity.

FIG. 2 schematically illustrates in simplified cross-sectional view a specific embodiment of the aforementioned method in which a dimer is synthesized on a substrate using a device similar to that illustrated in FIG. 1, but including a modifier reservoir 59 containing a surface modification fluid 60 having a fluid surface 61. FIG. 2A illustrates the ejection of a droplet 63 of surface modification fluid 60 selected to alter the wetting properties of a designated site on surface 51 of the substrate 45 where the dimer is to be synthesized. The ejector 33 is positioned by the ejector positioning means 43 below modifier reservoir 59 in order to achieve acoustic coupling therewith through acoustic coupling medium 41. Substrate 45 is positioned above the modifier reservoir 19 at a location that enables acoustic deposition of a droplet of surface modification fluid 60 at a designated site. Once the ejector 33, the modifier reservoir 59 and the substrate 45 are in proper alignment, the acoustic radiation generator 35 is activated to produce acoustic radiation that is directed by the focusing means 37 in a manner that enables ejection of droplet 63 of the surface modification fluid 60 from the fluid surface 61 onto a designated site on the underside surface 51 of the substrate. Once the droplet 63 contacts the substrate surface 51, the droplet modifies an area of the substrate surface to result in an increase or decrease in the surface energy of the area with respect to deposited fluids.

Figure 2A:
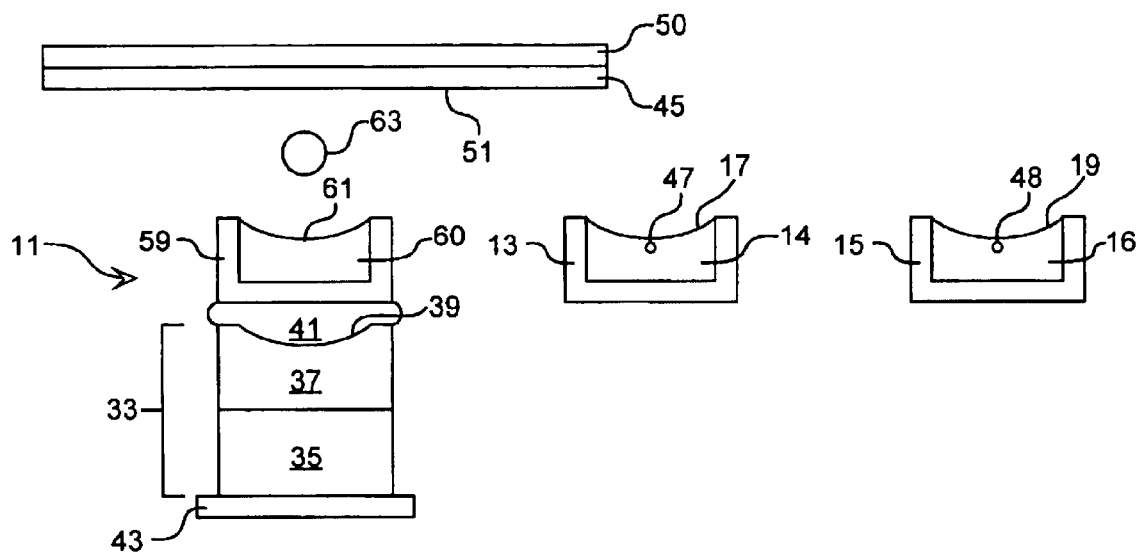
FIGS. 2A, 2B, 2C and 2D, collectively referred to as FIG. 2, schematically illustrate in simplified cross-sectional view an embodiment of the inventive method in which a dimer is synthesized in situ on a substrate using the device of FIG. 1.
Figure 2B:
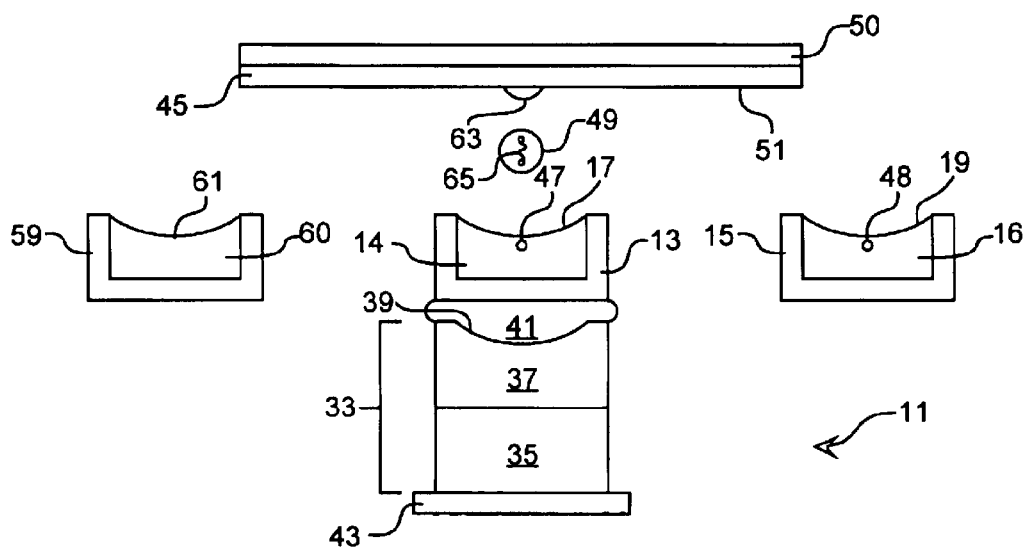

Then, as shown in FIG. 2B, the substrate 45 is repositioned by the substrate positioning means 50 such that the region of the substrate surface modified by droplet 63 is located directly over reservoir 13. FIG. 3B also shows that the ejector 33 is positioned by the ejector positioning means below reservoir 13 to acoustically couple the ejector and the reservoir through acoustic coupling medium 41. Once properly aligned, the ejector 33 is again activated so as to eject droplet 49 onto substrate. Droplet 49 contains a first monomeric moiety 65, preferably a biomolecule such as a protected nucleoside or amino acid, which after contact with the substrate surface attaches thereto by covalent bonding or adsorption.

Figure 2C:
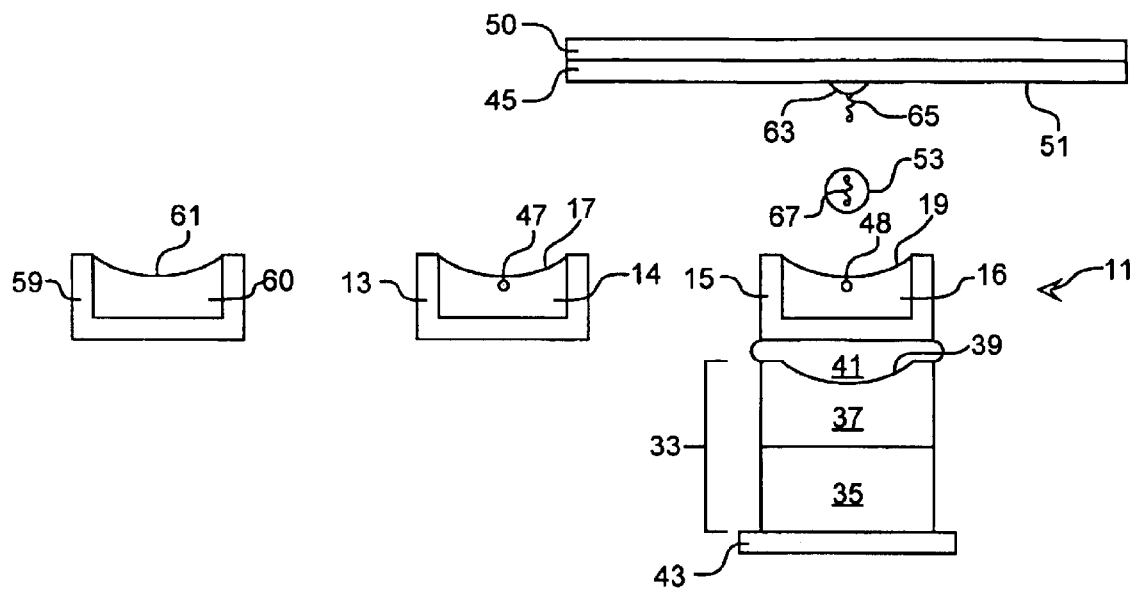
Figure 2D:
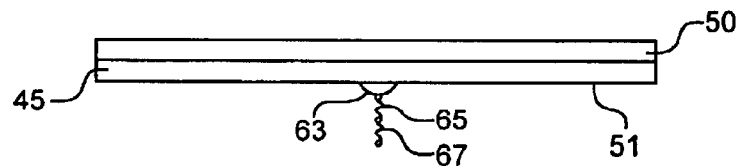

Then, as shown in FIG. 2C, the substrate 45 is again repositioned by the substrate positioning means 50 such that the site having the first monomeric moiety 65 attached thereto is located directly over reservoir 15 in order to receive a droplet therefrom. FIG. 3B also shows that the ejector 33 is positioned by the ejector positioning means below reservoir 15 to acoustically couple the ejector and the reservoir through acoustic coupling medium 41. Once properly aligned, the ejector 33 is again activated so as to eject droplet 53 is ejected onto substrate. Droplet 53 contains a second monomeric moiety 67, adapted for attachment to the first monomeric moiety 65, typically involving formation of a covalent bond so as to generate a dimer as illustrated in FIG. 3D. The aforementioned steps may be repeated to generate an oligomer, e.g., an oligonucleotide, of a desired length.

The chemistry employed in synthesizing substrate-bound oligonucleotides in this way will generally involve now-conventional techniques known to those skilled in the art of nucleic acid chemistry and/or described in the pertinent literature and texts. See, for example, *DNA Microarrays: A Practical Approach*, M. Schena, Ed. (Oxford University Press, 1999). That is, the individual coupling reactions are conducted under standard conditions used for the synthesis of oligonucleotides and conventionally employed with automated oligonucleotide synthesizers. Such methodology is described, for example, in D. M. Matteuci et al. (1980) *Tet. Lett.* 521:719, U.S. Pat. No. 4,500,707 to Caruthers et al., and U.S. Pat. Nos. 5,436,327 and 5,700,637 to Southern et al.

Alternatively, an oligomer may be synthesized prior to attachment to the substrate surface and then "spotted" onto a particular locus on the surface using the focused acoustic ejection methodology described in detail above. Again, the oligomer may be an oligonucleotide, an oligopeptide, or any other biomolecular (or nonbiomolecular) oligomer moiety. Preparation of substrate-bound peptidic molecules, e.g., in the formation of peptide arrays and protein arrays, is described in co-pending patent application U.S. Ser. No. 09/669,997 ("Focused Acoustic Energy in the Preparation of Peptidic Arrays"), inventors Mutz and Ellson, filed Sep. 25, 2000 and assigned to Picoliter, Inc. (Sunnyvale, Calif.). Preparation of substrate-bound oligonucleotides, particularly arrays of oligonucleotides wherein at least one of the oligonucleotides contains one or more partially nonhybridizing segments, is described in co-pending patent application U.S. Ser. No. 09/699,267 ("Arrays of Oligonucleotides Containing Nonhybridizing Segments"), inventor Ellson, also filed on Sep. 25, 2000 and assigned to Picoliter Inc. Preparation of other types of arrays using focused acoustic energy is described in co-pending patent application U.S.

Ser. No. 09/727,392, filed on Nov. 29, 2000 and also assigned to Picoliter Inc.

It will be appreciated by those in the art that the invention is useful in the preparation of high density combinatorial libraries containing a variety of synthetic, semi-synthetic or naturally occurring molecular moieties, insofar as focused acoustic energy makes possible the use and manipulation of extremely small volumes of fluids with extraordinary accuracy. This is in sharp contrast to prior techniques for preparing combinatorial libraries, with which effective spot-to-spot binding cannot be guaranteed. Furthermore, piezoelectric jet technologies are limited with respect to the fluids that may be used since high temperatures are required, while the present invention does not require high temperatures (although heat may be necessary in some cases, i.e., with fluids having high melting points) and thus allows for the possibility of using fluids that may be heat-sensitive or even flammable.

It should be evident, then, that many variations of the invention are possible. For example, each of the ejected droplets may be deposited as an isolated and "final" feature, e.g., in spotting oligonucleotides, as mentioned above. Alternatively, or in addition, a plurality of ejected droplets may be deposited on the same location of a substrate surface in order to synthesize a biomolecular array in situ, as described above. For array fabrication, it is expected that various washing steps may be used between droplet ejection steps. Such wash steps may involve, e.g., submerging the entire substrate surface on which features have been deposited in a washing fluid. In a modification of this process, the substrate surface may be deposited on a fluid containing a reagent that chemically alters all features at substantially the same time, e.g., to activate and/or deprotect biomolecular features already deposited on the substrate surface to provide sites on which additional coupling reactions may occur.

The focused acoustic energy methodology described herein enables ejection of droplets at a rate of at least about 1,000,000 droplets per minute from the same reservoir, and at a rate of at least about 100,000 drops per minute from different reservoirs. In addition, current positioning technology allows for the ejector positioning means to move from one reservoir to another quickly and in a controlled manner, thereby allowing fast and controlled ejection of different fluids. That is, current commercially available technology allows the ejector to be moved from one reservoir to another, with repeatable and controlled acoustic coupling at each reservoir, in less than about 0.1 second for high performance positioning means and in less than about 1 second for ordinary positioning means. A custom designed system will allow the ejector to be moved from one reservoir to another with repeatable and controlled acoustic coupling in less than about 0.001 second. In order to provide a custom designed system, it is important to keep in mind that there are two basic kinds of motion: pulse and continuous. Pulse motion involves the discrete steps of moving an ejector into position, emitting acoustic energy, and moving the ejector to the next position; again, using a high performance positioning means with such a method allows repeatable and controlled acoustic coupling at each reservoir in less than 0.1 second. A continuous motion design, on the other hand, moves the ejector and the reservoirs continuously, although not at the same speed, and provides for ejection during movement. Since the pulse width is very short, this type of process enables over 10 Hz reservoir transitions, and even over 1000 Hz reservoir transitions.

In order to ensure the accuracy of fluid ejection, it is important to determine the location and the orientation of the fluid surface from which a droplet is to be ejected with respect to the ejector. Otherwise, ejected droplets may be improperly sized or travel in an improper trajectory. Thus, another embodiment of the invention relates to a method for determining the height of a fluid surface in a reservoir between ejection events. The method involves acoustically coupling a fluid-containing reservoir to an acoustic radiation generator and activating the generator to produce a detection acoustic wave that travels to the fluid surface and is reflected thereby as a reflected acoustic wave. Parameters of the reflected acoustic radiation are then analyzed in order to assess the spatial relationship between the acoustic radiation generator and the fluid surface. Such an analysis will involve the determination of the distance between the acoustic radiation generator and the fluid surface and/or the orientation of the fluid surface in relationship to the acoustic radiation generator.

More particularly, the acoustic radiation generator may be activated so as to generate low energy acoustic radiation that is insufficiently energetic to eject a droplet from the fluid surface. This is typically done by using an extremely short pulse (on the order of tens of nanoseconds) relative to that normally required for droplet ejection (on the order of microseconds). By determining the time it takes for the acoustic radiation to be reflected by the fluid surface back to the acoustic radiation generator and then correlating that time with the speed of sound in the fluid, the distance—and thus the fluid height—may be calculated. Of course, care must be taken in order to ensure that acoustic radiation reflected by the interface between the reservoir base and the fluid is discounted. It will be appreciated by those of ordinary skill in the art that such a method employs conventional or modified sonar techniques.

Once the analysis has been performed, an ejection acoustic wave having a focal point near the fluid surface is generated in order to eject at least one droplet of the fluid, wherein the optimum intensity and directionality of the ejection acoustic wave is determined using the aforementioned analysis optionally in combination with additional data. The "optimum" intensity and directionality are generally selected to produce droplets of consistent size and velocity. For example, the desired intensity and directionality of the ejection acoustic wave may be determined by using not only the spatial relationship assessed as above, but also geometric data associated with the reservoir, fluid property data associated with the fluid to be ejected, and/or by using historical droplet ejection data associated with the ejection sequence. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal and/or rotational movement to allow appropriate focusing of the ejection acoustic wave.

In general, screening for the properties of the array constituents will be performed in a manner appropriate to the type of array generated. Screening for biological properties such as ligand binding or hybridization may be generally performed in the manner described in U.S. Pat. Nos. 5,744,305 and 5,445,934 to Fodor et al. U.S. Pat. Nos. 5,143,854 and 5,405,783 to Pirrung et al., and U.S. Pat. Nos. 5,700,637 and 6,054,270 to Southern et al. Screening a substrate for material properties may be effected by measuring physical and chemical properties by routine methods easily adaptable to microarrays. In addition to bulk material characteristics or properties, surface specific properties may be measured by surface specific physical techniques and physical techniques that are adapted to surface characterization. Macroscopic surface phenomena including adsorption, catalysis, surface reactions including oxidation, hardness, lubrication and friction, may be examined on a molecular scale using such characterization techniques. Various physical surface characterization techniques include without limitation diffractive techniques, spectroscopic techniques, microscopic surface imaging techniques, surface ionization mass spectroscopic techniques, thermal desorption techniques and ellipsometry. It should be appreciated that these classifications are arbitrary made for purposes of explication, and some overlap may exist.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains.

All patents, patent applications, journal articles and other references cited herein are incorporated by reference in their entireties.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

This example describes preparation of an array of oligonucleotides in the form of a library, and demonstrates the use of focused acoustic energy in the solid phase synthesis of oligonucleotides.

Microporous glass, preferably controlled pore size glass (CPG), is sintered onto the surface of a glass plate to form a CPG layer having a thickness sufficient to enable permeation to both the downward flow and the lateral wicking of fluids. Generally, a sufficient thickness is greater than about 10 $\mu$m.

Accordingly, the CPG is applied to the glass surface at a thickness of about 20 $\mu$m and the glass with powdered CPG resident thereon is heated at 750° C. for about 20 minutes then cooled. Commercially available microscope slides (BDH Super Premium 76×26×1 mm) are used as supports. Depending on the specific glass substrate and CPG material used the sintering temperature and time may be adjusted to obtain a permeable and porous layer that is adequately attached to the glass beneath while substantially maintaining the permeability to fluids and thickness of the microporous glass layer. The slides heated for 20 minutes with a 1 cm square patch of microporous glass applied at a pre-heating thickness of about 20 $\mu$m yield a sintered layer of substantially the same depth as pre-heating, namely 20 $\mu$m.

The microporous glass layer is derivatized with a long aliphatic linker that can withstand conditions required to deprotect the aromatic heterocyclic bases, i.e. 30% $NH_3$ at 55° C. for 10 hours. The linker, which bears a hydroxyl moiety, the starting point for the sequential formation of the oligonucleotide from nucleotide precursors, is synthesized in two steps. First, the sintered microporous glass layer is treated with a 25% solution of 3-glycidoxypropyltriethoxysilane in xylene containing several drops of Hunig's base as a catalyst in a staining jar fitted with a drying tube, for 20 hours at 90° C. The slides are then washed with MeOH, $Et_2O$ and air dried. Neat hexaethylene glycol and a trace amount of concentrated $H_2SO_4$ acid are then added and the mixture is kept at 80° C. for 20 hours. The slides are washed with MeOH, $Et_2O$, air dried and stored desiccated at –20° C. until use. (Preparative technique generally described in British Patent Application 8822228.6 filed Sep. 21, 1988.)

Focused acoustic ejection of about 0.24 pL of anhydrous acetonitrile (the primary coupling solvent) containing a fluorescent marker onto the microporous substrate is then shown to obtain a circular patch of about 5.6 $\mu$m diameter on the permeable sintered microporous glass substrate. The amount of acoustic energy applied at the fluid surface may be adjusted to ensure an appropriate diameter of chemical synthesis for the desired site density. 5.6 $\mu$m diameter circular patches are suitable for preparing an array having a site density of $10^6$ sites/$cm^2$ with the circular synthetic patches spaced 10 $\mu$m apart center to center, and the synthetic patches therefore spaced edge to edge at least 4 $\mu$m apart at the region of closest proximity. All subsequent spatially directed acoustically ejected volumes in this example are of about 0.24 pL; it will be readily appreciated that the ejection volumes can be adjusted for solutions other than pure acetonitrile by adjusting the acoustic energy as necessary for delivery of an appropriately sized droplet after spreading on the substrate (here about a 5 $\mu$m radius).

The oligonucleotide synthesis cycle is performed using a coupling solution prepared by mixing equal volumes of 0.5 M tetrazole in anhydrous acetonitrile with a 0.2 M solution of the required β-cyanoethylphosphoramidite, e.g. A-β-cyanoethylphosphoramidite, C-β-cyanoethylphosphoramidite, G-β-cyanoethylphosphoramidite, T(or U)-β-cyanoethylphosphoramidite. Coupling time is three minutes. Oxidation with a 0.1 M solution of $I_2$ in THF/pyridine/$H_2O$ yields a stable phosphotriester bond. Detritylation of the 5' end with 3% trichloroacetic acid (TCA) in dichloromethane allows further extension of the oligonucleotide chain. No capping step is required because the excess of phosphoramidites used over reactive sites on the substrate is large enough to drive coupling to completion. After coupling the slide the subsequent chemical reactions (oxidation with $I_2$, and detritylation by TCA) are performed by dipping the slide into staining jars. Alternatively the focused acoustic delivery of $I_2$ in THF/pyridine/$H_2O$ and/or 3% TCA in dichloromethane to effect the oxidation and tritylation steps only at selected sites may be performed if sufficient time transpires to permit evaporation of substantially all the solvent from the previous step so that the synthetic patch edges do not move outwards and closer to the neighboring synthetic patches, and further to provide an anhydrous environment for subsequent coupling steps if $I_2$ in THF/pyridine/$H_2O$ is delivered within the reaction chamber.

After the synthesis is complete, the oligonucleotide is deprotected in 30% $NH_3$ for 10 hours at 55° C. Because the coupling reagents are moisture-sensitive, and the coupling step must be performed under anhydrous conditions in a sealed chamber or container. This may be accomplished by performing the acoustic spotting in a chamber of desiccated gas obtained by evacuating a chamber that contains the acoustic ejection device and synthetic substrate and replacing the evacuated atmospheric gas with desiccated $N_2$ by routine methods; washing steps may be performed in the chamber or by removing the slide and washing it in an appropriate environment, for example, by a staining jar fitted with a drying tube. Because washing and other steps such as detritylation may be more conveniently carried out outside the chamber, the synthesis may also be performed in a controlled humidity room that contains the controlled atmosphere chamber in which the spotting is done, with the other steps carried out in the room outside the chamber. Alternatively, a controlled humidity room may be used for spotting with other steps carried out in less controlled environment by use of, for example, a staining jar fitted with a drying tube.

EXAMPLE 2

This example describes preparation of a peptide array in the form of a combinatorial library, and demonstrates the use of focused acoustic energy in the combinatorial solid phase synthesis of all tetramers that can be made from the 20 naturally occurring amino acids ($20^4$ or =160,000 amino acid sequences in all) in a quadruplicate array format. Four identical copies of the combinatorial array to be prepared are contained in a 1 cm×1 cm area nominally divided into four quadrants, each quadrant containing 250,000 synthesized sites of size 10 μm×10 μm arrayed in 500 rows and 500 columns. Only 400 rows and columns are used in each quadrant; the first and last 50 rows and columns are not used for synthesis, and function to space the four identical arrays from each other and the edges of the area, although alternative arrangement of the four identical arrays can obtain greater distance between arrays by moving each array closer to the corners of the square area. In addition to systematically generating the combinatorial sequences, deposition of the monomers employs a systematic method of ensuring that similar amino acid sequences are less likely to be spatially close. Although many such methods exist, with some requiring sophisticated computation, and can take into account side chain similarities in addition to identity, e.g. hydrophobic Val, Leu, Ile the scheme used relies on a basic sequential list of amino acids which is phase shifted as the row number increases. For example the 20 natural amino acids can be listed sequentially based on the alphabetic order of their single letter abbreviations, in which case: Ala (A) is "1"; Cys (C) is "2"; Asp (D) is 3; . . . Val (V) is "19"; and Trp (W) is "20".

For the first monomer deposited, in the first row in a given quadrant in which a peptide is synthesized, which is the $51^{st}$ nominal row in that quadrant, beginning with the first synthetic column ($51^{st}$ nominal column) amino acids (as activated for the synthesis described in more detail below) are deposited as the basic sequential list from 1 to 20 in alphabetical order of the one letter abbreviations. Beginning with the second synthetic row ($52^{nd}$ nominal row), the order is shifted by one position starting at "2" and returning to "1" after "20" (2, 3, 4, 5 . . . 19, 20, 1); thus for the quadruplicate spaced array arrangement being made, in the $52^{nd}$ nominal row (second synthetic row) of a given quadrant, the first amino acid deposited in the $51^{st}$ and $431^{st}$ nominal column of the $52^{nd}$ nominal row is "2" or Cys, and the amino acids deposited in the $68^{th}$ and $448^{th}$, $69^{th}$ and $449^{th}$, and $70^{th}$ and $450^{th}$ nominal columns of this row are 19, 20 and 1 respectively (V, W, A).

Additional monomers are added in the quadrants as follows, although numerous alternatives exist. For the second monomer in the first synthetic row ($51^{st}$ nominal row) the monomer deposition order for the second monomer is the same as for the first monomer in the first 20 synthetic columns (nominal 51–70) of this row, and the order is shifted by one for each successive group of 20 synthetic columns, thus the order is 2, 3 . . . 19, 20, 1 for nominal columns 71–90 (hereinafter denoted [71–90]-{2, 3 . . . 19, 20, 1}) and according to this notation: [91–110]-{3, 4 . . . 20, 1,2}; [111–130]-{4,5 . . . 1,2,3} . . . [431–450]-{20, 1 . . . 17, 18, 19}. For the second and third monomers in the second synthetic row ($52^{nd}$ nominal row) the monomer deposition order is shifted by one relative to the order for the underlying monomer in the first 20 synthetic columns (nominal 51–70) of this row, and the order is shifted by one for each successive group of 20 synthetic columns, thus for the second monomer the order is 3, 4 . . . 20, 1, 2 for nominal columns 51–70 and: [71–90]-{4, 5 . . . 1, 2, 3} [91–110]-{5, 6 . . . 2, 3, 4}; [111–130]-6, 7 . . . 3, 4, 5} . . . [431–450]-{2, 3 . . . 19, 20, 1}. Note that for the second monomer of the second synthetic row, the shift relative to the order of the first monomer in the first monomer in the first 20 columns of the first row ({1,2 . . . 18, 19, 20}), is 2 because one is the shift between subsequent monomers ($1^{st}$⇒$2^{nd}$; $2^{nd}$⇒$3^{rd}$) and the first monomer of the second synthetic row is shifted by one relative to the first monomer of the first synthetic row. For the second and third monomers in the third synthetic row ($53^{rd}$ nominal row) the monomer deposition order is shifted by two relative to the order for the underlying monomer in the first 20 synthetic columns (nominal 51–70) of this row, and the order is shifted by one for each successive group of 20 synthetic columns, thus the order for the second monomer is 5 . . . 20, 1, 2, 3, 4 for nominal columns 51–70 and: [71–90]-{6 . . . 1, 2, 3, 4, 5}, [91–110]{7, . . . 2,3,4, 5, 6}, [111–130]-{8, . . . 4,5, 6,6, 7} . . . [431–450]-{4, . . . 19, 20, 1, 2, 3}. For the second monomer in the Nth synthetic row (nominal row=50+N) the monomer deposition order for the second monomer is shifted by (N−1) relative to the order for the first monomer in the first 20 synthetic columns (nominal 51–70) of this row, and the order is shifted by one for each successive group of 20 synthetic columns, thus (for (k*N+a) >20, (k*N+a) is shifted as beginning with N+a−20*I, where I is the integer dividend of the quotient of (k*N+a) and 20, representing number of cycles with each integral multiple of 20 representing unshifted) the order for the second monomer is (2*N−1), 2*N . . . (2*N−3), (2*N−2) for nominal columns 51–70 and: [71–90]-{(2*N . . . (2*N−2), (2*N−1)}, [91–110]-{(2*N+1), (2*N+2) . . . (2*N−1), 2*N}, [111–130]-{(2*N+2), (2*N+3) . . . 2*N, (2*N+1)} . . . [431–450]-{(2*N−2), (2*N−1). . . (2*N−4), (2*N−3)}. Thus for the second monomer in the $400^{th}$ synthetic row ($450^{th}$ nominal row) the monomer deposition order for the second monomer begins with 19 (799–780) is circularly shifted by 18 relative to the order for the first monomer in the first 20 synthetic columns (nominal 51–70) of the first row, and the order is shifted by one for each successive group of 20 synthetic columns, thus the order is 19, 20 . . . (17), (18) for nominal columns 51–70 and: [71–90]-{20, 1 . . . 17, 18, 19}, [91–110]-{1, 2 . . . 18, 19, 20}, [111–130]-{2, 3 . . . 19, 20, 1} . . . [431–450]-{20, 1 . . . 17, 18, 19}. Note that for the second monomer of the Nth synthetic row, the shift relative to the order of the first monomer in the in the first 20 synthetic columns of the first row ({1, 2 . . . 18, 19, 20}), is 2*(N−1) because (N−1) is the shift between subsequent monomers ($1^{st}$⇒$2^{nd}$; $2^{nd}$⇒$3^{rd}$) and the first monomer of a synthetic row N is shifted by (N−1) relative to the first monomer of the first synthetic row.

The synthetic chemical steps are modified from known solid phase synthetic techniques (as described, for example, in Geysen et al., International Patent Application PCT/AU84/00039, published as WO 84/83564) that are adapted from the pioneering solid phase peptide synthesis of Merrifield et al. ((1965) *Nature* 207:(996):522–23; (1965) *Science* 150(693)178–85; (1966) *Anal. Chem.* 38(13):1905–14; (1967) *Recent. Prog. Horm. Res.* 23:451–82). The conventional methods of solid phase peptide synthesis as taught in these seminal papers are described in detail in Ericksen, B. W. and Merrifield, R. B. (1973) *The Proteins* 2:255–57 Academic Press, New York, and Meinhofer, J. (1976) *The Proteins* 2:45–267 Academic Press, New York. Briefly, all these methods add amino acid monomers protected by tert-butoxycarbonyl (t-butoxycarbonyl, t-Boc) at their amino groups, including their alpha amino groups ($N^\alpha$) to a nascent peptide that is attached to the substrate at the carboxy-terminal (C-terminal). The carbonyl moiety of the $N^\alpha$-t-Boc amino acid to be added to the peptide is activated to convert the hydroxyl group of the carboxylic moiety into an effective leaving group, resembling an acid anhydride in reactivity, using dicyclohexylcarbodiimide (DCC) to permit nucleophilic displacement by the terminal N of the nascent peptide to form a peptide bond that adds the monomer to the forming peptide. The newly added monomer has an N-terminus protected from further reaction by t-Boc, which is removed with trifluoroacetic acid (TFA), rendering the terminal amino group protonated, followed by deprotonation of the terminal amino group with triethylamine (TEA) to yield the reactive free amino group suitable for addition of another monomer.

The substrate employed is polyethylene, although the classic substrate for solid phase peptide synthesis, divinylbenzene cross-linked polystyrene chloromethylated by Friedel-Crafts reaction of the polystyrene resin on approximately one in four aromatic rings, could also be employed. Preparation of the polyethylene substrate, described in Geysen et al., International Patent Application PCT/AU84/00039, published as WO 84/83564, involves γ-ray irradiation (1 mrad dose) of polyethylene immersed in aqueous acrylic acid (6% v/v) to yield reactive polyethylene polyacrylic acid (PPA), according to the method of Muller-Schulte et al. (1982) *Polymer Bulletin* 7:77–81. $N^\alpha$-t-Boc-Lysine methyl ester is then coupled to the PPA by the Lysine ε-amino side chain. After deprotection of the $N^\alpha$ by removal of the t-Boc with TFA followed by TEA, DCC/$N^\alpha$-t-Boc-Alanine is added to couple t-Boc-Ala to the $N^\alpha$ of the Lys, thereby forming a peptide like $N^\alpha$-t-Boc-Ala-Lys-ε-N-PPA linker to which the DCC activated $N^\alpha$-t-Boc-amino acid monomers can be sequentially added to form the desired polymers upon deprotection of the $N^\alpha$ group of the $N^\alpha$-t-Boc-Ala.

For an array format, and to increase the effective surface area for polymer formation and enhance adhesion of acoustically ejected reagent droplets to the synthetic substrate, polyethylene fiber sheet material, approximate thickness 25 μm, available commercially and prepared by conventional methods is heat or fusion bonded according to routine methods to a smooth polyethylene backing approximately 0.15 cm thick to form a polyethylene fiber coated rough permeable substrate. The fiber coated sheet s cut into strips having the approximate dimensions of a commercial slide, and γ-irradiated (1 mrad) in 6% v/v aqueous acrylic acid to form the PPA activated substrate. The substrate must be adequately dried because the t-Boc protected and DCC activated reagents are water sensitive, and water contamination of acids applied to the synthetic sites, such as TFA application can hydrolyze the peptide bond. Thus anhydrous synthetic conditions are required throughout. Conventional drying of the substrate is effected with warm dry air at atmospheric or subatmospheric pressure by routine methods, specifically, the slides are washed with MeOH, $Et_2O$, air dried and stored desiccated at −20° C. until use.

The sequential combinatorial addition of monomers is performed as described above with all sites spotted with the appropriate DCC/$N^\alpha$-t-Boc-amino acid. The appropriate volume for acoustic ejection is as above. This yields a quasi-parallel synthesis because the spotting of different sites is not simultaneous, but the can be modified to synthesize the desired peptides only at some sites and synthesize at other sites later. The actual synthesis requires anhydrous organic solvent washing steps to remove unreacted activated amino acids or TFA or TEA, for a total of 11 steps per monomer addition. Thus a completely sequential synthesis would increase the number of steps performed for synthesizing an array drastically, but, for example synthesizing only at every other site in a first synthetic round and then synthesizing in a second session would improve array quality and only double the number of steps. To ensure that peptides are only formed at the chosen sites, the $N^\alpha$-t-Boc-Ala-Lys-ε-N-PPA linker can be selectively deprotected to expose the $N^\alpha$ of Ala only at chosen sites, by selective acoustic energy directed ejection of TFA onto the desired sites, followed by washing and selective application of TEA, followed by washing to effect, for example, selective deprotection of every other site.

The basic quasi-parallel combinatorial synthesis of all tetra-peptides that can be made from the naturally occurring amino acids may be performed in 44 steps excluding substrate preparation. As no selective linker deprotection is required, the substrate is immersed in TFA in a staining jar fitted with a drying tube, then washed, and immersed in TEA, and washed again, all under anhydrous conditions. The synthesis must be carried so that ejection of the fluid droplets occurs in a controlled atmosphere that is at minimum dry, and inert to the reagents used. This may be obtained by performing the acoustic spotting in a chamber of desiccated gas obtained by evacuating a chamber that contains the acoustic ejection device and synthetic substrate and replacing the evacuated atmospheric gas with desiccated $N_2$ by routine methods; washing steps may be performed in the chamber or by removing the slide and washing it in an appropriate environment, for example, by a staining jar fitted with a drying tube. Because washing and other steps such as detritylation may be more conveniently carried out outside the chamber, the synthesis may also be performed in a controlled humidity room that contains the controlled atmosphere chamber in which the spotting is done, with the other steps carried out in the room outside the chamber. Alternatively, a controlled humidity room may be used for spotting with other steps carried out in less controlled environment by use of, for example, a staining jar fitted with a drying tube.

Use of pre-synthesized short oligopeptides can also be used in lieu of amino acid monomers. Since focused acoustic ejection enables the rapid transition from the ejection of one fluid to another, many oligopeptides can be provided in small volumes on a single substrate (such as a microtiter plate) to enable faster assembly of amino acid chains. For example, all possible peptide dimers may be synthesized and stored in a well plate of over 400 wells. Construction of the tetramers can than be accomplished by deposition of only two dimers per site and a single linking step. Extending this further, a well plate with at least 8000 wells can be used to construct peptides with trimers.

EXAMPLE 3

Combinatorial methods of the preceding Examples 1 and 2 can be adapted to form combinatorial arrays of polysaccharides according to the instant invention. In oligosaccharides, the monosaccharide groups are normally linked via oxy-ether linkages. Polysaccharide ether linkages are difficult to construct chemically because linking methods are specific for each sugar employed. The ether oxygen linking group is also susceptible to hydrolysis by non-enzymatic chemical hydrolysis. Thus, there are no known methods of automated syntheses for ether linked carbohydrates, and conventional methods of making combinatorial arrays are not sufficiently flexible to permit combinatorial arrays of polysaccharides. The flexibility of acoustic spotting can be adapted to form oxy-ether linkage based combinatorial arrays by analogy to the alternative method of selective deblocking that may be employed for making the arrays of Examples 1 and 2. That is, the specific chemical methods for forming the linkage between any pair of sugars may be conveniently selected so that a different solution is ejected for adding a glucose to a specific terminal sugar of the forming polysaccharide, such as fructose, than is ejected for adding glucose to a different terminal sugar, such as ribose, without increasing the number of steps involved as would be the case with photolithographic synthesis, and might be the case with parallel printing of multiple reagents through conventional multi nozzle ink-jet type printers. The resulting polysaccharides remain susceptible to hydrolysis.

Polysaccharides may be synthesized in solution rather than the solid phase, as can the biomolecules made in the preceding examples, and the acoustic ejection of droplets can effect the solution syntheses of arrayed polysaccharides at high density on a substrate without any attachment during polymer formation by selective application of deblocking reagents to different sites. In situ solid phase synthesis is more readily adaptable to automation of even oxy-ether linkage based polysaccharides because at least the deblocking steps may be done simultaneously for all sites, although the susceptibility of the different linkages to hydrolysis may affect overall yield for different monomer sequences differently. Recently, methods of replacing the oxy-ether with a thio-ether linkage (U.S. Pat. Nos. 5,780,603 and 5,965,719) and with an amide linkage with the N atom linked to the anomeric C of the sugar (U.S. Pat. No. 5,756,712) have been introduced. The solid phase synthetic methods of the thio-ether linkage methods may be directly adapted to form high density combinatorial arrays in an analogous manner as techniques for the Merrifield peptide synthesis. Similarly, the amide linkage based polysaccharides may be adapted for solid phase high density array formation by employing, for example the thioether based substrate linkage taught in U.S. Pat. Nos. 5,780,603 and 5,965,719, or an amide linkage to an appropriate moiety functionalized surface by analogy to the linkage of U.S. Pat. No. 5,756,712.

Only the thioether based substrate linkage will be exemplified in detail, and this linkage will be used to make thioether (amide based oligosaccharides may be made analogously by reference to U.S. Pat. No. 5,756,712 with a thioether, or other, substrate linkage) based combinatorial array of oligosaccharides. The classic substrate for solid phase peptide synthesis, divinylbenzene cross-linked polystyrene chloromethylated by Friedel-Crafts reaction of the polystyrene resin on approximately one in four aromatic rings is employed, although a polyethylene substrate may be substituted.

Spun polystyrene sheet made by conventional methods or obtained commercially is heat or fusion bonded to a polystyrene backing to yield a porous permeable layer of spun polystyrene of approximately 25 $\mu$m thickness. The appropriate extent of crosslinking and chloromethylation is effected by conventional chemical synthetic methods as required. The thickness of the permeable layer will be appreciated to affect the dimensions of the area of actual chemical synthesis, as more vertical wicking room will result in less lateral spread of the acoustically deposited reagents. It also will be appreciated that the extent of crosslinking may be adjusted to control the degree of swelling, and softening upon application of organic solvents, and that the fibrous nature of the porous, permeable layer of spun polystyrene provides relatively more synthetic surface per nominal surface area of the substrate than provided by beads, thus less swelling is required to expand synthetic area to polymer sites inside the fibers. The substrate is aminated by conventional chemical synthetic methods, washed and stored desiccated at −20° C. until use.

The linking of a sugar to this substrate is first effected. Succinic anhydride (1.2 equivalents) is added to a solution of 1,2:3,4-di-O-isopropylidene-D-galactopyranose (1 equivalent) in pyridine at room temperature. The reaction is stirred overnight then concentrated in vacuo to yield 1,2:3,4-di-O-isopropylidene-6-O-(3-carboxy)propanoyl-D-galactopyranose. 80% aqueous acetic acid is added to the residue to remove the isopropylidene groups. When this reaction is complete, the reaction mixture is concentrated in vacuo. Excess 1:1 acetic anhydride/pyridine is then added to the residue to form 1,2,3,4-O-acetyl-6-O-(3-carboxy)propanoyl-D-galactopyranose, to which excess thiolacetic acid in dry dichloromethane under argon at 0° C. and $BF_3$ etherate is then added. The cold-bath is removed after 10 minutes. After 24 h the mixture is diluted with dichloromethane, washed with saturated sodium bicarbonate, dried over sodium sulfate, and concentrated to yield 1-S-acetyl-2,3,4-tri-O-acetyl-6-O-(3-carboxy) propanoyl-1-thio-α-D-galactopyranose. The aminated polystyrene (Merrifield resin) substrate is contacted with the 1-S-acetyl-2,3,4-tri-O-acetyl-6-O-(3-carboxy)propanoyl-1-thio-α-D-galactopyranose and a carbodiimide coupling reagent to afford the O,S-protected galactopyranose coupled to the substrate through the 6-O-(3-carboxy)propanoyl group.

The preceding substrate is used for combinatorial synthesis of thioether linked polysaccharides based on thiogalactose derivatives. Nine copies of the combinatorial array of all possible trimers of four monomeric 1-thiogalactose derivatives ($4^3$=64 in all) are synthesized on a total substrate surface area of 1 $cm^2$ divided into square synthetic sites 333 $\mu$m×333 $\mu$m, corresponding to a site density of 1000 sites/$cm^2$. This arrangement permits a 3 site or 999$^{\mu m}$ spacing between each copy of the array in each axis of the array plane. A 25 pL droplet of fluorescent solvent deposited on the described porous permeable spun polystyrene on polystyrene substrate yields a spot of about 56 $\mu$m diameter, and a 100 pL droplet yields a spot of about 112 $\mu$m diameter (cylindrical shaped spot wicked into depth of porous substrate with about ½ of porous layer occupied by solid polystyrene and little swelling thereof).

Step A—Synthesis of 1-Dithioethyl-2,3,4,6-tetra-O-acetyl-galactopyranoside:

1-Thio-2,3,4,6-tetra-O-acetyl-galactopyranoside (500 mg, 1.37 mmol) and diethyl-N-ethyl-sulfenylhydrazidodicarboxylate (360 mg, 2.0 mmol) (prepared by known methods as described by Mukaiyama et al. (1968) *Tetrahedron Letters* 56:5907–8) are dissolved in dichloromethane (14 mL) and stirred at room temperature. After 10 min, the solution is concentrated and column chromatography ($SiO_2$, hexane/ethylacetate 2:1) yields 1-dithioethyl-2,3,4,6-tetra-O-acetyl-galactopyranoside (580 mg, quant) as a white solid ($R_f$ 0.27 in hexanes/ethyl acetate (2:1)).$^1$H-NMR (360 MHZ, $CHCl_3$): .δ 1.30 (dd, 3H, J=7.4 Hz, $CH_3$), 1.96, 2.02, 2.03, 2.13 (4 s, 12H, $4CH_3CO$), 2.79 (ddd, 2H, J=7.4 Hz, J=7.4 Hz, J=1.3 Hz, $CH_2$), 3.94 (ddd, 1H, $J_4,5$=1.0 Hz, $J_5,6a$=6.6 Hz, $J_5,6b$=7.6 Hz, 5-H), 4.10 ddd, 2H, 61-H, 6b-H), 4.51 (d, 1H, $J_1,2$=10.0 Hz, 1-H), 5.05 (dd, 1H, $J_2,3$=10.0 Hz, $J_3,4$=3.3 Hz, 3-H)), 5.38 (dd, 1H, $J_1,2$=10.0 Hz, $J_3,3$=10.0 Hz, 2-H), 5.40 (dd, 1H, $J_3,4$=3.3 Hz, $J_4,5$=1.0 Hz, 4-H); m/z calculated for $C_{16}H_{24}O_9S_2$ (M+Na) 447.1, found 447.0.

Step B—Synthesis of 1-dithioethyl-β-D-galactopyranoside:

1-Dithioethyl-2,3,4,6-tetra-O-acetyl-galactopyranoside from Step A (500 mg, 1.18 mmol) is dissolved in dry methanol (10 mL) and treated with methanolic sodium methoxide (1 M, 150 μL). After 2 h, the solution is neutralized with Amberlite 1R-120 ($H^+$) resin, filtered and concentrated to give 1-dithioethyl-6-β-D-galactopyranoside as a white solid (300 mg, quant).

Step C—Coupling of 1-Dithioethyl-β-D-galactopyranoside to the Substrate:

1-Dithioethyl-6-O-D-galactopyranoside (200 mg, 780 μmol) is dissolved in dry pyridine (8 mL), and DMAP (5 mg) is added to the mixture, which is maintained at 60° C. throughout.

Of the total (9×64=576) sites used to form the 9 duplicate arrays, and in each duplicate array of 64 sites of actual synthesis, ¼ (16 per array, 144 total) of the array sites are patterned with the 1-dithioethyl-6-β-D-galactopyranoside/DMAP. in dry pyridine. This solution is acoustically ejected onto the substrate at the desired locations. Dry controlled atmospheric conditions, namely a dry inert gas environment, are also used for this oligosaccharide synthesis. The appropriate volume deposited at each site is determined by test deposition at some of the array sites, taking into consideration that the synthetic area should be wholly contained in the synthetic site, and too much dead space is preferably avoided. About 10 to 100 pL droplet volumes are found to be appropriate, and 100 pL is spotted onto the sites where the first monomer is desired to be 1-dithioethyl-6-β-D-galactopyranoside. The substrate is as described, spun polystyrene resin on a polystyrene backing (trityl chloride-resin, loading 0.95 mmol/g of active chlorine, polymer matrix: copolystyrene-1% DVB) is heated for 24 h at 60° C. The resin is filtered off, and washed successively with methanol, tetrahydrofuran, dichloromethane and diethyl ether (10 mL each) to afford 1-dithioethyl-6-β-D-galactopyranoside covalently linked to the trityl resin through the hydroxyl group in the 6-position at the desired sites.

Step D—Patterning Additional 1-Dithioethyl-6-pyranosides:

It will be readily appreciated that this step can be practiced with other 1-dithioethyl-6-pyranosides as desired to be linked to the substrate. ¼ of the sites of each of the duplicate arrays are spotted with a solution for linking 1-dithioethyl-6-β-D-glucopyranoside in about the same volume as deposited in Step C, ¼ are spotted to yield the 1-dithioethyl-6-β-D-mannopyranoside, and the remaining ¼ are spotted to yield the 1-dithioethyl-6-β-D-allopyranoside.

Step E—Generation of the Free Thiol on the Substrate:

The substrate sites from Step C spotted with dry tetrahydrofuran (THF) in the area of 1-dithioethyl-6-pyranoside deposition (about 4 pL per pL deposited in Step C). Dry methanol (about ¾ pL per pL deposited in Step C), dithiothreitol (about 185 picograms) and triethylamine (about ½ pL per pL deposited in Step C) are deposited at desired synthetic areas of the combinatorial sites by acoustic deposition and the sites are allowed to react under the specified controlled atmosphere conditions for about 10 minutes to an hour at room temperature. The entire substrate is washed by immersion in an adequate volume, successively, of methanol, tetrahydrofuran, dichloromethane and diethyl ether. Micro-FTIR (of substrate deposition sites): 2565 $cm^{-1}$ (SH stretch). Alternatively, if selective generation of the free thiol is not desired, the substrate may be treated on the whole of the surface as follows: 8 ml dry THF is applied to the surface of the substrate which is placed in a shallow container just large enough to contain the substrate, 1.2 ml dry ethanol, 256 mg dithiothreitol, and 0.8 ml triethylamine are added to the THF and the container is shaken for about 10 hours at room temperature under the described conditions.

Step F—Michael Addition Reaction:

The substrate from Step E is again placed in the shallow container of Step E and swollen in dry N,N-dimethylformamide (4 mL) and then cyclohept-2-en-1-one (280 μl, 252 μmol) is added and the container is shaken at room temperature. After 2 hours, the liquid is removed and the substrate is washed successively with methanol, tetrahydrofuran, dichloromethane and diethyl ether (40 mL each). Alternatively if selective Michael addition is desired, the desired sites may be selectively spotted in the area of synthesis: N,N-dimethylformamide (about 2.5 pL per pL deposited in Step C); cyclohept-2-en-1-one (about 0.2 pL, 0.2 picomole per pL deposited in Step C). The selectively spotted sites are allowed to react under the specified controlled atmosphere conditions for about 10 minutes to an hour at room temperature prior to the specified washing steps.

Step G—Reductive Amination with an Amino Acid:

The substrate from Step F is again placed in the shallow container of preceding steps and swollen in dichloromethane (4 mL). Glycine tert-butyl ester hydrochloride (150 mg, 1,788 μmol), sodium sulfate (400 mg), sodium triacetoxyborohydride (252 mg, 1188 μmol) and acetic acid (40 μL) are added at room temperature under argon atmosphere and the container shaken for 24 hours. The liquid is removed and the substrate is washed successively with washed successively with water, methanol, tetrahydrofuran and dichloromethane.

Additional monomers may be added by repetition of the preceding steps with the desired 1-dithioethyl-6-pyranosides. It will be readily appreciated that this step can be practiced with 1-dithioethyl-6-β-D-galactopyranoside/DMAP and the other 1-dithioethyl-6-pyranoside/DMAP desired for linking to the substrate. The desired sites of each of the duplicate arrays are selectively spotted with the appropriate 1-dithioethyl-6-pyranoside/DMAP solution for linking in about the same volume as deposited in Step C (1-dithioethyl-6-β-D-mannopyranoside/DMAP, 1-dithioethyl-6-β-D-allopyranoside/DMAP, and 1-dithioethyl-6-β-D-glucopyranoside/DMAP).

EXAMPLE 4

Combinatorial arrays of alloys can readily be prepared using the methodology of the invention. Molten metals are acoustically ejected onto array sites on a substrate. No monomer sequence exists for metals, but the composition of the alloys may be altered by deposition of more of a given metal at a certain site without problems associated with polymer elongation; the problem with deposition of more metal droplets of the same volume to form different compositions is that array density must be decreased to accommodate the most voluminous composition made, as the size of droplets is not conveniently adjusted over wide ranges of droplet volume. An additional reason to reduce array density in alloy formation is that with alloys it is often desirable to form a material that has a bulk and surface, rather than a film which has a surface but not a bulk and therefore the properties of the thin-layer "surface" are not the same as the surface of the bulk material (see generally Somorjai, *Surface Chemistry and Catalysis*, supra).

As may be readily appreciated, an infinite number of compositions of any two metals exist. Composition in terms of combinatorial synthesis of arrays of alloys by acoustic ejection of fluid is complicated by the volumetric acoustic ejection being different for different molten metals having different densities and interatomic interactions, but the different stoichiometric compositions generated correspond to different combinations of metal and number of droplets deposited are reproducible, e.g. an alloy of 5 droplets of Sn ejected at an energy, $E_1$ and five droplets of Cu ejected at $E_1$ or $E_2$ will have the same compositions when duplicated under the same conditions, and the stoichiometric composition of alloys of interest can always be determined by SIMS. To promote uniform alloy formation it is desirable to spot all the droplets of molten metal to be deposited onto a site in rapid succession rather than waiting for a droplet to solidify before depositing another, although such combinatorial "stacks" are also of potential interest. As it is most convenient not to change acoustic energy between deposition of droplets, the same energy is most conveniently used for ejecting different metals, and the stoichiometric and other, including surface properties of the material so generated may be determined later and reproduced by exact duplication of the synthetic process. The molten metals must be at an appropriate temperature (T) above its melting point to ensure that the droplet is still molten when it reaches the substrate. In addition to an inert gas environment, which may be appreciated to be important if making alloys rather than stacks of oxidized metal salts is desired, to prevent oxidation of the metals especially at the surface of the droplets, a gas with low heat capacity is preferable to high heat capacity gases. In addition, the temperature of the substrate and the distance between the substrate and the fluid meniscus may be adjusted to ensure molten material reaching the substrate and remaining molten for sufficient time to permit alloying with subsequently deposited droplets. Furthermore, after a given alloy composition is made at a given array site, both the ejection energy and the meniscus to substrate distance may require adjustment in light of the foregoing considerations, as is readily appreciated.

A convenient systematic combinatorial approach involves selecting a number of molten compositions for ejection and a total number of droplets deposited at each site. Array density of $10^5$ sites/cm² is convenient as each site is conveniently a 100 μm square, an area which can be easily appreciated to accommodate 10, approximately picoliter (pL) sized, droplets, because 10 pL spread uniformly over the area of the site would be only 1 μm, deep, and gravity prevents such complete spreading and low surface angle.

For 4 different molten metallic compositions available for ejection and 10 droplets, it may easily be demonstrated that 342 possible compositions exist, and likewise for 15 droplets, 820 possible compositions exist in terms of droplet number. For d droplet compositions with m ejected metals (although the molten ejection vessel contents need not be a pure metal, and may themselves be an alloy):

$$^dQ_m = {}_{n=1 \to m}\Sigma(S(m)_n)*(Z(m,d)_n)$$

$^dQ_m$ is defined as # metal compositions for d=# droplets, m=# of molten compositions available to be ejected; $S(m)_n$ is the # of unique sets having n members of the m available molten compositions; $Z(n,d)_n$ is # of d droplet combinations of n used of the m available for deposition, corresponding to $S(m)_n$. Further:

$$Z(m,d)_n = {}_{i=1 \to C(n,d)}\Sigma O(n,d)_i$$

$CS(n,d)_i$ denotes ith set of coefficients for n components that add to d droplets, with $C(n,d)$, representing the total number of coefficient sets satisfying this requirement; $O(n,d)_i$ is the number of possible orderings of the ith set of n coefficients for d droplets corresponding to $CS(n,d)_i$.

For example, for d=10, m=4, let the 4 vessels contain, respectively, Sn, In, Cd and Zn.

1 metal compositions (n=1):

$Z(4,10)_1 = {}_{i=1 \to C(1,10)}\Sigma O(1,10)_i = 1*1$, because the only possible coefficient is 10, and it can be ordered in only one way. The corresponding $S(4)_1$ is 4, as 4 unique sets of 1 metal can be chosen for ejection.

2 metal compositions (n=2):

The corresponding $S(4)_2$ is 6, as [4!/2!]/2! unique sets of 2 metals can be chosen for ejection. The C(2,10) unique sets of 2 non-negative, nonzero coefficients that add to 10, such as (9,1) and the corresponding O (2,10)$_i$ are [denoted by the notation $\{CS(2,10)_1:O(2,10)_1, CS(2,10)_2, 1:O(2,10)_2 \ldots CS(2,10)_{C(n,d)}:O(2,10)_{C(n,d)}\}$]:

$\{(9,1):2, (8,2):2, (7,3):2, (6,4):2, (5,5):1\}; \Rightarrow Z(4,10)_2 = {}_{i=1 \to C(2,10)}\Sigma O(2,10)_i = 2+2+2+2+1=9$.

3 metal compositions:

The corresponding $S(4)_3$ is 4 ([4!/1!]/3!), 4 unique sets of 3 metals can be chosen for ejection. The C(3,10) unique sets of 3 non-negative, nonzero coefficients that add to 10 are: $\{(8,1,1):3, (7,2,1):6, (6,3,1):6, (6,2,2):3, (5,4,1):6, (5,3,2):6, (4,4,2):3, (4,3,3):3\}; \Rightarrow$ $Z(4,10)_3 = {}_{i=1 \to C(3,10)}\Sigma O(3,10)i = 3+6+6+3+6+6+3+3=36$.

4 metal compositions:

The corresponding $S(4)_4$ is 1 (4!/4!), as 1 unique sets of 4 metals can be chosen for ejection. The C(4,10) unique sets of 4 non-negative, nonzero coefficients that add to 10 are: $\{(7,1,1,1):4, (6,2,1,1):12, (5,3,1,1):12, (5,2,2,1):12, (4,4,1,1):6, (4,3,2,1):24, (4,4,2,2):6, (3,3,3,1):4, (3,3,2,2):6\}; \Rightarrow$ $Z(4,10)_4 = {}_{i=1 \to C(4,10)}\Sigma O(4,10)i = 4+12+12+12+6+24+6+4+6=86$.

From the preceding:

$^{10}Q_4 = {}_{n=1 \to 4}\Sigma(S(4)_n)*(Z(4,10)_n) = 4*1+6*9+4*36+1*86 = 288$.

An appropriate substrate for the alloy array of acoustically deposited molten metallic compositions is made of sintered alumina by conventional methods or obtained commercially. An array of Sn (mp=281.8° C.), In (mp=156.6° C.), Cd (mp=320.9° C.) and Zn (mp=419.6° C.) components (e.g. pure ejected molten metal compositions) is formed by acoustic deposition of 15 droplets/array site on a sintered alumina substrate. Thickness of the substrate is about 0.25 cm, to withstand the heat. The site density is chosen to allow all possible droplet compositions that can be made from four metals with 15 droplets, 820 possible compositions including, for example (in droplets): 14(Sn), 1*(In); 12Sn, 1In, 1Cd, 1Zn; 1Sn, 12In, 1Cd, 1Zn. These compositions and the 901 remaining compositions may be obtained as above demonstrated for 10 droplet compositions of four components. The chosen density is 1000 sites/cm2, corresponding to a nominal site size of 333×333 μm, and permitting the complete collection of compositions to be made on a 1 cm² area. Duplicate copies of the array are made on a commercial microscope slide sized strip of substrate, separated by ½ cm to permit the convenient separation of the two identical arrays.

The acoustic energy is adjusted to yield an average droplet volume of about 1 pL, and 15 droplet ejection that does not exceed the 333×333 μm square area provided for the site, under the desired conditions, including atmosphere pressure and composition, length of droplet flight, substrate temperature. After the average droplet size is adjusted to about one pL, 15 droplets of each metal are acoustically ejected onto a site and the ejection energy is adjusted downwards if any of these pure sites exceed the margins of the site. Enough sites exist for all 820 possible compositions to be ejected onto each 1 cm square array after using up to 96 of the available 1000, sites for calibration, but the single ejected component sites so created may function as the single composition sites if sufficiently the localized region within which the alloy resides similar to the other sites in dimension, as dimensions affect cooling and a substantially different geometry would not be precisely the same material.

Although the actual volumes ejected of the different molten components may be adjusted to be equal by using a different acoustic energy of ejection, more rapid ejection is possible if the ejection energy is held constant. It is readily apprehended that if too wide a discrepancy exists between the droplet volumes ejected for each component, that the overall geometry of the cooling composition could vary widely depending on its makeup, but this is not the case for the metals being deposited here, because both their densities and factors determining interatomic interactions in the molten state, such as polarizability, are sufficiently similar. In all cases the conditions for the formation of the alloy at a given site are always reproducible, and the actual composition and other physical properties of the composition may be ascertained by physical methods including all described surface physical characterization methods.

Because of the toxicity of Cd, the acoustic deposition of the molten metals is carried out in a separate atmospherically controlled low humidity chamber under Ar gas to reduce undesired reactions and cooling. Higher heat capacity inert gases and more reactive gases, such as $O_2$, and $O_2$/hydrocarbons may be used for experiments under different conditions, but may require adjustment of the distance between the fluid meniscus and substrate or the temperature of the molten reagent to be ejected or both to ensure that the droplet reaches the substrate in a molten state.

After calibration the first duplicate array is spotted by acoustic ejection as described onto a substrate maintained at a temperature of 125° C. Each of the 820 possible 15 droplet compositions is made by sequentially depositing fifteen droplets at each site, the 15 droplets deposited according to the different coefficient arrangements described above. The metals are maintained at a known temperature that is sufficiently greater than the mp of the metal that the ejected droplet arrives at the substrate surface molten under the conditions, including distance of flight and pressure, temperature and heat capacity of the atmosphere. The droplets are deposited at each site lowest melting metal first in order of increasing melting temperature with the highest melting temperature metal deposited last, e.g., In, Sn, Cd, Zn, so that successive droplets of higher melting temperature metal will melt any solidified material. The procedure is repeated at different substrate temperatures at 5 degree intervals until arrays formed with substrate temperature ranging from 40° C. to 425° C. are formed.

We claim:

1. A method for generating an array of molecular moieties on a porous substrate surface divided into a plurality of discrete surface sites, the method comprising applying focused acoustic energy to each of a plurality of a reservoirs each containing a molecular moiety in a fluid, wherein the focused acoustic energy is applied using an acoustic ejector comprised of an acoustic radiation generator and a focusing means in a manner effective to eject a droplet from each reservoir toward the substrate surface such that the molecular moiety in each droplet attaches to a localized region within a different surface site.

2. The method of claim 1, wherein each molecular moiety is different.

3. The method of claim 2, wherein a droplet is ejected toward each surface site, such that every surface site has a molecular moiety attached thereto.

4. The method of claim 3, wherein each molecular moiety is different.

5. The method of claim 1, wherein the molecular moieties are biomolecules.

6. The method of claim 5, wherein the biomolecules are nucleotidic.

7. The method of claim 6, wherein the biomolecules are oligonucleotides.

8. The method of claim 7, wherein the biomolecules are nucleotidic monomers, and the method further comprises stepwise synthesis of an oligonucleotide within each surface site by repeated deposition of individual nucleotidic monomers at each site using focused acoustic energy.

9. The method of claim 5, wherein the biomolecules are peptidic.

10. The method of claim 3, wherein the porous substrate surface is comprised of at least 62,500 discrete surface sites.

11. The method of claim 10, wherein the porous substrate surface is comprised of at least 250,000 discrete surface sites.

12. The method of claim 11, wherein the porous substrate surface is comprised of at least 1,000,000 discrete surface sites.

13. The method of claim 12, wherein the porous substrate surface is comprised of at least 1,500,000 discrete surface sites.

* * * * *